(12) United States Patent
Sakamoto et al.

(10) Patent No.: US 9,212,170 B2
(45) Date of Patent: Dec. 15, 2015

(54) 4-ALKANOYLAMINO-3-PYRAZOLONE DERIVATIVE

(71) Applicant: Daiichi Sankyo Company, Limited, Tokyo (JP)

(72) Inventors: Atsunobu Sakamoto, Tokyo (JP); Naoki Tanaka, Tokyo (JP); Takeshi Fukuda, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/495,052

(22) Filed: Sep. 24, 2014

(65) Prior Publication Data

US 2015/0011552 A1    Jan. 8, 2015

Related U.S. Application Data

(63) Continuation of application No. PCT/JP2013/059656, filed on Mar. 29, 2013.

(30) Foreign Application Priority Data

Mar. 30, 2012    (JP) ................. 2012-079858

(51) Int. Cl.

| C07D 403/04 | (2006.01) |
| C07D 401/14 | (2006.01) |
| C07D 401/04 | (2006.01) |
| A61K 31/4439 | (2006.01) |
| A61K 31/415 | (2006.01) |
| C07C 59/01 | (2006.01) |
| A61K 9/00 | (2006.01) |
| A61K 47/10 | (2006.01) |
| A61K 9/20 | (2006.01) |
| A61K 9/48 | (2006.01) |

(52) U.S. Cl.
CPC ............ *C07D 403/04* (2013.01); *A61K 9/0019* (2013.01); *A61K 9/2018* (2013.01); *A61K 9/4866* (2013.01); *A61K 31/415* (2013.01); *A61K 31/4439* (2013.01); *A61K 47/10* (2013.01); *C07C 59/01* (2013.01); *C07D 401/04* (2013.01); *C07D 401/14* (2013.01)

(58) Field of Classification Search
CPC .. C07D 403/04; C07D 401/14; C07D 401/04; A61K 31/4439; A61K 31/415
See application file for complete search history.

(56) References Cited

U.S. PATENT DOCUMENTS

| 8,067,407 | B2 | 11/2011 | Jeske et al. |
| 8,252,817 | B2 | 8/2012 | Flamme et al. |
| 8,580,778 | B2 | 11/2013 | Jeske et al. |
| 9,085,572 | B2 | 7/2015 | Flamme et al. |
| 2009/0269420 | A1 | 10/2009 | Jeske et al. |
| 2010/0035906 | A1 | 2/2010 | Flamme et al. |
| 2010/0093803 | A1 | 4/2010 | Thede et al. |
| 2010/0305085 | A1 | 12/2010 | Thede et al. |
| 2011/0112103 | A1 | 5/2011 | Kuribayashi et al. |
| 2011/0294788 | A1 | 12/2011 | Altenburger et al. |
| 2011/0301148 | A1 | 12/2011 | Altenburger et al. |
| 2012/0035151 | A1 | 2/2012 | Jeske et al. |
| 2012/0322772 | A1 | 12/2012 | Flamme et al. |
| 2014/0038938 | A1 | 2/2014 | Jeske et al. |

FOREIGN PATENT DOCUMENTS

| CN | 101213189 A | 7/2008 |
| CN | 102015685 A1 | 4/2011 |
| CN | 102066337 A | 5/2011 |
| DE | 10 2007 044 032 A1 | 3/2009 |
| JP | 2008-539180 A | 11/2008 |
| JP | 2010-507602 A | 3/2010 |
| JP | 2010-507605 A | 3/2010 |
| JP | 2011-088840 A | 5/2011 |
| JP | 2011-105708 A | 6/2011 |
| JP | 2011-518794 A | 6/2011 |
| WO | WO-2009/131129 A1 | 10/2009 |

(Continued)

OTHER PUBLICATIONS

Database Registry Chemical Abstracts Service, Columbus, Ohio, Accession No. RN 929293-74-3, RN 929293-75-4, RN 929293-78-7, Entered STN: Apr. 6, 2007.*

International Search Report dated May 7, 2013 issued in Application No. PCT/JP2013/059656.

Kralj, et al., "Reactions of methyl 2-acetylamino-3-(dimethylamino)propenoate with hydrazines," Slovenski Kemijski Dnevi, 11th, Maribor, Solvenia, Sep. 23-23, Univerza v Mariboru, Fakulteta za Kemijo in Kemijsko Tehnologijo, Maribor, Solvenia., Sep. 2005, p. 1/5-5/5.

Warshakoon, et al., "Design and synthesis of a series of novel pyrazolopyridines as HIF 1-α prolyl hydroxylase inhibitors," Biorganic & Medicinal Chemistry Letters, 2006, vol. 16, pp. 5687-5690.

(Continued)

*Primary Examiner* — Samantha Shterengarts
(74) *Attorney, Agent, or Firm* — Foley & Lardner LLP

(57) ABSTRACT

The present invention provides a compound which enhances the production of erythropoietin. The present invention provides, for example, a compound represented by the formula (1) wherein $R^1$: $-Q^1$, $-Q^1-X-Q^2$, or $-Q^1-X-Q^2-Y-Q^3$: a monocyclic or bicyclic aromatic heterocyclic group; $Q^2$, $Q^3$: an aromatic hydrocarbon ring group or a monocyclic aromatic heterocyclic group; X: —CONH—, —CONHCH$_2$—, —CH$_2$OCH$_2$—, —NHCH$_2$CH$_2$—, or the like; Y: a single bond, —O—, —(CH$_2$)$_n$—, or —O—(CH$_2$)$_n$—; m, n: an integer from 1 to 3; $R^2$: H or an alkyl group; and $R^3$: H, an alkoxycarbonyl group, a carboxy group, an aromatic hydrocarbon ring group, or a monocyclic aromatic heterocyclic group.

34 Claims, No Drawings

(56) References Cited

FOREIGN PATENT DOCUMENTS

| WO | WO-2010/076524 A2 | 7/2010 |
| WO | WO-2010/076525 A1 | 7/2010 |

OTHER PUBLICATIONS

Chinese Office Action issued in corresponding Application No. 201380028513.7.

* cited by examiner

4-ALKANOYLAMINO-3-PYRAZOLONE DERIVATIVE

CROSS REFERENCE TO RELATED APPLICATIONS

The present invention is a continuation of PCT/JP2013/059656, filed Mar. 29, 2013, which claims priority to Japanese Application No. 2012-079858, filed Mar. 30, 2012, both of which are incorporated herein by reference.

TECHNICAL FIELD

The present invention relates to low molecular weight compounds having an erythropoietin production-enhancing activity.

BACKGROUND ART

Erythropoietin (hereinafter abbreviated as EPO) is a glycoprotein hormone that is essential for erythrocyte hematopoiesis. It is normally secreted from the kidneys and promotes production of erythrocytes by acting on erythrocyte stem cells present in bone marrow. In diseases presenting with a decrease in intrinsic EPO production (such as chronic renal failure), since erythrocyte production decreases and symptoms of anemia are exhibited, treatment is provided in the form of replacement therapy using gene-recombinant human EPO. However, this gene-recombinant human EPO has been indicated as having shortcomings such as being a biological preparation and associated with expensive health care costs, having poor convenience due to being an injection and having antigenicity.

On the other hand, for example, pyrazole derivatives substituted at the 4-position with a carboxy group (see Non Patent Document 1), 3-pyrazolone derivatives substituted at the 4-position with an aromatic heterocyclic group (see Patent Documents 1 to 6), and 4,5-fused 3-pyrazolone derivatives (Patent Document 7), are known to be low molecular weight EPO inducers. 3-pyrazolone derivatives substituted at the 4-position with an alkanoylamino group have not yet been known.

CITATION LIST

Patent Documents

Patent Document 1: German Patent Application Publication No. 10 2007 044 032
Patent Document 2: U.S. Patent Application Publication No. 2009/0269420
Patent Document 3: U.S. Patent Application Publication No. 2010/0035906
Patent Document 4: U.S. Patent Application Publication No. 2010/0093803
Patent Document 5: U.S. Patent Application Publication No. 2010/0305085
Patent Document 6: U.S. Patent Application Publication No. 2011/0294788
Patent Document 7: U.S. Patent Application Publication No. 2011/0301148

Non Patent Document

Non Patent Document 1: Bioorganic & Medicinal Chemistry Letters, 2006, Vol. 16, p. 5687-5690

SUMMARY OF INVENTION

Technical Problem of the Invention

The inventors of the present invention conducted studies for the purpose of providing novel low molecular weight compounds that have a superior EPO production-enhancing activity and that are useful for the treatment of diseases caused by decreased EPO, and for the purpose of providing a medicament containing such compounds.

Means for Solution to the Problem

In order to solve the aforementioned problems, the inventors of the present invention found that novel compounds having a 4-alkanoylamino-3-pyrazolone structure have a superior EPO production-enhancing activity and that they are effective for treating diseases caused by decreased EPO, thereby leading to completion of the present invention.

According to the present invention, novel 4-alkanoylamino-3-pyrazolone compounds represented by the following general formula (1) or pharmacologically acceptable salts thereof (hereinafter collectively referred to as compounds of the present invention), are provided.

Specifically, the present invention provides:
(1) a compound represented by the following general formula (1):

[Formula 1]

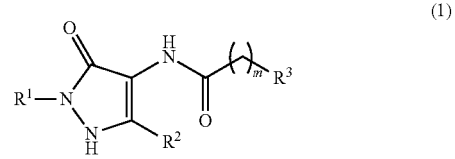

(1)

or a pharmacologically acceptable salt thereof,
wherein
$R^1$ represents a group represented by $-Q^1$, $-Q^1-X-Q^2$, or $-Q^1-X-Q^2-Y-Q^3$;
$Q^1$ represents a monocyclic or bicyclic aromatic heterocyclic group which may have 1 or 2 substituents independently selected from substituent group α;
substituent group α represents the group consisting of a halogen atom, a $C_1-C_6$ alkyl group, a halo $C_1-C_6$ alkyl group, a $C_1-C_6$ alkoxy group, a $C_3-C_7$ cycloalkyl group, and a 4- to 7-membered heterocycloalkyl group;
$Q^2$ represents an aromatic hydrocarbon ring group which may have 1 or 2 substituents independently selected from substituent group β, or a monocyclic aromatic heterocyclic group which may have 1 or 2 substituents independently selected from substituent group β;
substituent group β represents the group consisting of a halogen atom, a $C_1-C_6$ alkyl group, a halo $C_1-C_6$ alkyl group, a $C_1-C_6$ alkoxy group, a $C_3-C_7$ cycloalkyl group, and a cyano group;
$Q^3$ represents an aromatic hydrocarbon ring group which may have 1 or 2 substituents independently selected from substituent group γ, or a monocyclic aromatic heterocyclic group which may have 1 or 2 substituents independently selected from substituent group γ;
substituent group γ represents the group consisting of a halogen atom, a $C_1-C_6$ alkyl group, a halo $C_1-C_6$ alkyl group, a $C_1-C_6$ alkoxy group, a $C_3-C_7$ cycloalkyl group, and a cyano group;

X represents a single bond, —(CH$_2$)$_n$—, —CH=CH—, —CONH—, —NHCO—, —CONHCH$_2$—, —NHCOCH$_2$—, —CH$_2$NHCO—, —CH$_2$CONH—, —SO$_2$NH—, —CH$_2$OCH$_2$—, or —NHCH$_2$CH$_2$—;

Y represents a single bond, —O—, —(CH$_2$)$_n$—, or —O—(CH$_2$)$_n$—;

m and n each independently represents an integer from 1 to 3;

R$^2$ represents a hydrogen atom or a C$_1$-C$_6$ alkyl group; and

R$^3$ represents a hydrogen atom, a C$_1$-C$_6$ alkoxycarbonyl group, a carboxy group, an aromatic hydrocarbon ring group, or a monocyclic aromatic heterocyclic group, (2) a compound or a pharmacologically acceptable salt thereof according to (1), wherein R$^2$ is a hydrogen atom or a methyl group, (3) a compound or a pharmacologically acceptable salt thereof according to (1) or (2), wherein R$^3$ is a hydrogen atom, a methoxycarbonyl group, an ethoxycarbonyl group, a propoxycarbonyl group, a tert-butoxycarbonyl group, a carboxy group, a phenyl group, or a pyridyl group, (4) a compound or a pharmacologically acceptable salt thereof according to (1) or (2), wherein R$^3$ is a hydrogen atom, a tert-butoxycarbonyl group, or a carboxy group, (5) a compound or a pharmacologically acceptable salt thereof according to (1) or (2), wherein R$^3$ is a hydrogen atom, (6) a compound or a pharmacologically acceptable salt thereof according to any one of (1) to (5), wherein m is 1 or 2, (7) a compound or a pharmacologically acceptable salt thereof according to any one of (1) to (6), wherein R$^1$ is a group represented by -Q$^1$, and Q$^1$ is a pyridyl group, a pyrimidinyl group, a pyrazinyl group, a pyridazinyl group, a quinolyl group, an isoquinolyl group, or a quinazolinyl group which may have 1 or 2 substituents independently selected from substituent group α, (8) a compound or a pharmacologically acceptable salt thereof according to any one of (1) to (6), wherein R$^1$ is a group represented by -Q$^1$, and Q$^1$ is a pyridyl group or a pyrimidinyl group which may have 1 or 2 substituents independently selected from substituent group α, (9) a compound or a pharmacologically acceptable salt thereof according to (7) or (8), wherein the substituent group α is the group consisting of a fluorine atom, a chlorine atom, a bromine atom, a methyl group, a methoxy group, a morpholinyl group, and a piperidinyl group,

(10) a compound or a pharmacologically acceptable salt thereof according to (7) or (8), wherein the substituent group α is the group consisting of a morpholinyl group and a piperidinyl group,

(11) a compound or a pharmacologically acceptable salt thereof according to any one of (1) to (6), wherein R$^1$ is a group represented by -Q$^1$-X-Q$^2$ or -Q$^1$-X-Q$^2$-Y-Q$^3$, and Q$^1$ is a pyridyl group, a pyrimidinyl group, a pyrazinyl group, a pyridazinyl group, a quinolyl group, an isoquinolyl group, or a quinazolinyl group which may have 1 or 2 substituents independently selected from substituent group α,

(12) a compound or a pharmacologically acceptable salt thereof according to any one of (1) to (6), wherein R$^1$ is a group represented by -Q$^1$-X-Q$^2$ or -Q$^1$-X-Q$^2$-Y-Q$^3$, and Q$^1$ is a pyridyl group or a pyrimidinyl group which may have 1 or 2 substituents independently selected from substituent group α,

(13) a compound or a pharmacologically acceptable salt thereof according to (11) or (12), wherein the substituent group α is the group consisting of a fluorine atom, a chlorine atom, a methyl group, and a methoxy group,

(14) a compound or a pharmacologically acceptable salt thereof according to any one of (11) to (13), wherein Q$^2$ is a phenyl group, a pyridyl group, a pyrimidinyl group, a pyrazinyl group, or a pyridazinyl group which may have 1 or 2 substituents independently selected from substituent group β,

(15) a compound or a pharmacologically acceptable salt thereof according to any one of (11) to (13), wherein Q$^2$ is a phenyl group or a pyridyl group which may have 1 or 2 substituents independently selected from substituent group β,

(16) a compound or a pharmacologically acceptable salt thereof according to (14) or (15), wherein the substituent group β is the group consisting of a fluorine atom, a chlorine atom, a bromine atom, a methyl group, an ethyl group, a propyl group, an isopropyl group, a butyl group, an isobutyl group, a sec-butyl group, a tert-butyl group, a trifluoromethyl group, a cyclohexyl group, and a cyano group,

(17) a compound or a pharmacologically acceptable salt thereof according to (14) or (15), wherein the substituent group β is the group consisting of a chlorine atom, a bromine atom, a tert-butyl group, a trifluoromethyl group, and a cyclohexyl group,

(18) a compound or a pharmacologically acceptable salt thereof according to any one of (11) to (17), wherein X is —CH$_2$—, —CH$_2$CH$_2$—, —CH=CH—, —CONH—, —CONHCH$_2$—, —CH$_2$OCH$_2$—, or —NHCH$_2$CH$_2$—,

(19) a compound or a pharmacologically acceptable salt thereof according to any one of (11) to (17), wherein X is —CH$_2$—, —CH$_2$CH$_2$—, —CONH—, —CONHCH$_2$—, or —CH$_2$OCH$_2$—,

(20) a compound or a pharmacologically acceptable salt thereof according to any one of (11) to (19), wherein R$^1$ is a group represented by -Q$^1$-X-Q$^2$-Y-Q$^3$, and Q$^3$ is a phenyl group, a pyridyl group, a pyrimidinyl group, a pyrazinyl group, or a pyridazinyl group which may have 1 or 2 substituents independently selected from substituent group γ,

(21) a compound or a pharmacologically acceptable salt thereof according to any one of (11) to (19), wherein R$^1$ is a group represented by -Q$^1$-X-Q$^2$-Y-Q$^3$, and Q$^3$ is a phenyl group or a pyridyl group which may have 1 or 2 substituents independently selected from substituent group γ,

(22) a compound or a pharmacologically acceptable salt thereof according to (20) or (21), wherein the substituent group γ is the group consisting of a fluorine atom, a chlorine atom, a bromine atom, a methyl group, an ethyl group, a propyl group, an isopropyl group, a trifluoromethyl group, and a cyano group,

(23) a compound or a pharmacologically acceptable salt thereof according to (20) or (21), wherein the substituent group γ is the group consisting of a chlorine atom, a bromine atom, a trifluoromethyl group, and a cyano group,

(24) a compound or a pharmacologically acceptable salt thereof according to any one of (11) to (23), wherein Y is a single bond or —O—,

(25) a compound or a pharmacologically acceptable salt thereof according to (1), selected from the following:
6-(4-acetamido-5-oxo-2,5-dihydro-1H-pyrazol-1-yl)-N-(4-cyclohexylphenyl)nicotinamide,
6-(4-acetamido-5-oxo-2,5-dihydro-1H-pyrazol-1-yl)-N-(4-tert-butylphenyl)nicotinamide,
6-(4-acetamido-5-oxo-2,5-dihydro-1H-pyrazol-1-yl)-N-(3-tert-butylphenyl)nicotinamide,
6-(4-acetamido-5-oxo-2,5-dihydro-1H-pyrazol-1-yl)-N-[4-(trifluoromethyl)phenyl]nicotinamide, 6-(4-acetamido-5-oxo-2,5-dihydro-1H-pyrazol-1-yl)-N-(4-chlorophenyl)nicotinamide,
N-[2-(6-morpholin-4-ylpyrimidin-4-yl)-3-oxo-2,3-dihydro-1H-pyrazol-4-yl]acetamide,
N-[3-oxo-2-(6-piperidin-1-ylpyrimidin-4-yl)-2,3-dihydro-1H-pyrazol-4-yl]acetamide,
N-(2-{5-[(benzyloxy)methyl]pyridin-2-yl}-3-oxo-2,3-dihydro-1H-pyrazol-4-yl)acetamide,
N-(3-oxo-2-{6-[(2-phenylethyl)amino]pyrimidin-4-yl}-2,3-dihydro-1H-pyrazol-4-yl)acetamide,
N-(2-{4-[(benzyloxy)methyl]pyridin-2-yl}-3-oxo-2,3-dihydro-1H-pyrazol-4-yl)acetamide,
6-(4-acetamido-5-oxo-2,5-dihydro-1H-pyrazol-1-yl)-N-(biphenyl-3-ylmethyl)nicotinamide,
6-(4-acetamido-5-oxo-2,5-dihydro-1H-pyrazol-1-yl)-N-[(2'-cyanobiphenyl-4-ylmethyl)]nicotinamide,
N-[2-(5-{[(2'-cyanobiphenyl-4-yl)methoxy]methyl}pyridin-2-yl)-3-oxo-2,3-dihydro-1H-pyrazol-4-yl]acetamide,
N-(2-{5-[(biphenyl-4-ylmethoxy)methyl]pyridin-2-yl}-3-oxo-2,3-dihydro-1H-pyrazol-4-yl)acetamide,
N-(2-{5-[(biphenyl-3-ylmethoxy)methyl]pyridin-2-yl}-3-oxo-2,3-dihydro-1H-pyrazol-4-yl)acetamide,
6-(4-acetamido-3-methyl-5-oxo-2,5-dihydro-1H-pyrazol-1-yl)-N-[4-(trifluoromethyl)phenyl]nicotinamide,
6-(4-acetamido-3-methyl-5-oxo-2,5-dihydro-1H-pyrazol-1-yl)-N-(4-chlorophenyl)nicotinamide,
6-(4-acetamido-3-methyl-5-oxo-2,5-dihydro-1H-pyrazol-1-yl)-N-(4-bromophenyl)nicotinamide,
6-(4-acetamido-3-methyl-5-oxo-2,5-dihydro-1H-pyrazol-1-yl)-N-(4-tert-butylphenyl)nicotinamide,
6-(4-acetamido-3-methyl-5-oxo-2,5-dihydro-1H-pyrazol-1-yl)-N-(6-phenylpyridin-3-yl)nicotinamide,
N-[2-(5-{[(2'-cyanobiphenyl-4-yl)methoxy]methyl}pyridin-2-yl)-5-methyl-3-oxo-2,3-dihydro-1H-pyrazol-4-yl]acetamide,
tert-butyl 4-[(5-methyl-3-oxo-2-{5-[(6-phenylpyridyl-3-yl)carbamoyl]pyridin-2-yl}-2,3-dihydro-1H-pyrazol-4-yl)amino]-4-oxobutanoate,
4-[(5-methyl-3-oxo-2-{5-[(6-phenylpyridyl-3-yl)carbamoyl]pyridin-2-yl}-2,3-dihydro-1H-pyrazol-4-yl)amino]-4-oxobutanoic acid,
N-{5-methyl-3-oxo-2-[5-({[4-(trifluoromethyl)benzyl]oxy}methyl)pyridin-2-yl]-2,3-dihydro-1H-pyrazol-4-yl}acetamide,
N-(5-methyl-3-oxo-2-{5-[4-(trifluoromethyl)benzyl]pyridin-2-yl}-2,3-dihydro-1H-pyrazol-4-yl)acetamide,
N-[5-methyl-3-oxo-2-(5-{2-[4-(trifluoromethyl)phenyl]ethyl}pyridin-2-yl)-2,3-dihydro-1H-pyrazol-4-yl]acetamide, and
N-[5-methyl-3-oxo-2-(5-{(E)-2-[4-(trifluoromethyl)phenyl]ethenyl}pyridin-2-yl)-2,3-dihydro-1H-pyrazol-4-yl]acetamide,

(26) a compound or a pharmacologically acceptable salt thereof according to (1), selected from the following:
6-(4-acetamido-5-oxo-2,5-dihydro-1H-pyrazol-1-yl)-N-(4-cyclohexylphenyl)nicotinamide,
6-(4-acetamido-5-oxo-2,5-dihydro-1H-pyrazol-1-yl)-N-(4-tert-butylphenyl)nicotinamide,
6-(4-acetamido-5-oxo-2,5-dihydro-1H-pyrazol-1-yl)-N-(3-tert-butylphenyl)nicotinamide,
6-(4-acetamido-5-oxo-2,5-dihydro-1H-pyrazol-1-yl)-N-[4-(trifluoromethyl)phenyl]nicotinamide,
6-(4-acetamido-5-oxo-2,5-dihydro-1H-pyrazol-1-yl)-N-(4-chlorophenyl)nicotinamide,
N-[2-(6-morpholin-4-ylpyrimidin-4-yl)-3-oxo-2,3-dihydro-1H-pyrazol-4-yl]acetamide,
N-[3-oxo-2-(6-piperidin-1-ylpyrimidin-4-yl)-2,3-dihydro-1H-pyrazol-4-yl]acetamide,
N-(2-{5-[(benzyloxy)methyl]pyridin-2-yl}-3-oxo-2,3-dihydro-1H-pyrazol-4-yl)acetamide,
N-(2-{4-[(benzyloxy)methyl]pyridin-2-yl}-3-oxo-2,3-dihydro-1H-pyrazol-4-yl)acetamide,
6-(4-acetamido-5-oxo-2,5-dihydro-1H-pyrazol-1-yl)-N-(biphenyl-3-ylmethyl)nicotinamide,
N-[2-(5-{[(2'-cyanobiphenyl-4-yl)methoxy]methyl}pyridin-2-yl)-3-oxo-2,3-dihydro-1H-pyrazol-4-yl]acetamide,
N-(2-{5-[(biphenyl-4-ylmethoxy)methyl]pyridin-2-yl}-3-oxo-2,3-dihydro-1H-pyrazol-4-yl)acetamide,
N-(2-{5-[(biphenyl-3-ylmethoxy)methyl]pyridin-2-yl}-3-oxo-2,3-dihydro-1H-pyrazol-4-yl)acetamide,
6-(4-acetamido-3-methyl-5-oxo-2,5-dihydro-1H-pyrazol-1-yl)-N-(4-tert-butylphenyl)nicotinamide,
N-[2-(5-{[(2'-cyanobiphenyl-4-yl)methoxy]methyl}pyridin-2-yl)-5-methyl-3-oxo-2,3-dihydro-1H-pyrazol-4-yl]acetamide,
N-{5-methyl-3-oxo-2-[5-({[4-(trifluoromethyl)benzyl]oxy}methyl)pyridin-2-yl]-2,3-dihydro-1H-pyrazol-4-yl}acetamide,
N-(5-methyl-3-oxo-2-{5-[4-(trifluoromethyl)benzyl]pyridin-2-yl}-2,3-dihydro-1H-pyrazol-4-yl)acetamide, and
N-[5-methyl-3-oxo-2-(5-{2-[4-(trifluoromethyl)phenyl]ethyl}pyridin-2-yl)-2,3-dihydro-1H-pyrazol-4-yl]acetamide,

(27) a pharmaceutical composition containing as an active ingredient a compound or a pharmacologically acceptable salt thereof according to any one of (1) to (26) above,
(28) a pharmaceutical composition according to (27) above, for the prophylaxis and/or treatment of anemia,
(29) a pharmaceutical composition according to (28) above, wherein the anemia is nephrogenic anemia, anemia of prematurity, anemia incidental to chronic diseases, anemia incidental to cancer chemotherapy, cancerous anemia, inflammation-associated anemia, or anemia incidental to congestive heart failure,
(30) a pharmaceutical composition according to (28) above, wherein the anemia is anemia incidental to chronic kidney disease,
(31) a pharmaceutical composition according to (27) above, for producing erythropoietin,
(32) use of a compound or a pharmacologically acceptable salt thereof according to any one of (1) to (26) above, for producing a medicament,
(33) use according to (32) above, wherein the medicament is a medicament for the prophylaxis and/or treatment of anemia,
(34) use according to (33) above, wherein the anemia is nephrogenic anemia, anemia of prematurity, anemia incidental to chronic diseases, anemia incidental to cancer chemotherapy, cancerous anemia, inflammation-associated anemia, or anemia incidental to congestive heart failure,
(35) use according to (33) above, wherein the anemia is anemia incidental to chronic kidney disease,
(36) a method for producing erythropoietin, comprising: administering a pharmacologically effective amount of a compound or a pharmacologically acceptable salt thereof according to any one of (1) to (26) above to a mammal or bird,
(37) a method for the prophylaxis and/or treatment of a disease, comprising: administering a pharmacologically effective amount of a compound or a pharmacologically acceptable salt thereof according to any one of (1) to (26) above to a mammal,
(38) a method according to (37) above, wherein the disease is anemia,

(39) a method according to (37) above, wherein the disease is nephrogenic anemia, anemia of prematurity, anemia incidental to chronic diseases, anemia incidental to cancer chemotherapy, cancerous anemia, inflammation-associated anemia, or anemia incidental to congestive heart failure,
(40) a method according to (37) above, wherein the disease is anemia incidental to chronic kidney disease,
(41) a method according to any one of (37) to (40) above, wherein the mammal is a human,
(42) a compound or a pharmacologically acceptable salt thereof according to any one of (1) to (26) above, for use in a method for the treatment or prophylaxis of a disease,
(43) a compound or a pharmacologically acceptable salt thereof according to (42) above, wherein the disease is anemia,
(44) a compound or a pharmacologically acceptable salt thereof according to (42) above, wherein the disease is nephrogenic anemia, anemia of prematurity, anemia incidental to chronic diseases, anemia incidental to cancer chemotherapy, cancerous anemia, inflammation-associated anemia, or anemia incidental to congestive heart failure, and
(45) a compound or a pharmacologically acceptable salt thereof according to (42) above, wherein the disease is anemia incidental to chronic kidney disease.

The compounds of the present invention represented by the aforementioned general formula (1) have a 4-alkanoylamino-3-pyrazolone skeleton. A substituent at the 2-position of the pyrazolone ring has 1 to 4 cyclic groups, and these cyclic groups have a specific substituent. The compounds of the present invention or pharmacologically acceptable salts thereof have a superior EPO production-enhancing activity.

The following provides an explanation of substituents in the compounds of the present invention.

A "halogen atom" in the definitions of substituent group α, substituent group β, and substituent group γ refers to a fluorine atom, a chlorine atom, a bromine atom, or an iodine atom, preferably a chlorine atom or a bromine atom.

A "$C_1$-$C_6$ alkyl group" in the definitions of substituent group α, substituent group β, substituent group γ, and $R^2$ refers to a straight or branched chain alkyl group having 1 to 6 carbon atoms. Examples include a methyl group, an ethyl group, a propyl group, an isopropyl group, a butyl group, an isobutyl group, a sec-butyl group, a tert-butyl group, a pentyl group, an isopentyl group, a 2-methylbutyl group, a neopentyl group, a 1-ethylpropyl group, a hexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group, a 1,2-dimethylbutyl group, a 1,3-dimethylbutyl group, a 2,3-dimethylbutyl group, and a 2-ethylbutyl group. The $C_1$-$C_6$ alkyl group in substituent group α, substituent group β, and substituent group γ is preferably a tert-butyl group. The $C_1$-$C_6$ alkyl group in $R^2$ is preferably a methyl group.

A "halo $C_1$-$C_6$ alkyl group" in the definitions of substituent group α, substituent group β, and substituent group γ refers to a group in which 1 to 7 hydrogen atoms on the carbon atom(s) of a straight or branched chain alkyl group having 1 to 6 carbon atoms are replaced with aforementioned "halogen atom(s)". Examples include a fluoromethyl group, a chloromethyl group, a bromomethyl group, a difluoromethyl group, a dichloromethyl group, a dibromomethyl group, a trifluoromethyl group, a trichloromethyl group, a tribromomethyl group, a 2,2,2-trifluoroethyl group, a 2,2,2-trichloroethyl group, a 2-fluoroethyl group, a 2-chloroethyl group, a 2-bromoethyl group, a 2-iodoethyl group, a 3-chloropropyl group, a 4-fluorobutyl group, a 6-iodohexyl group, and a 2,2-dibromoethyl group. The halo $C_1$-$C_6$ alkyl group is preferably a trifluoromethyl group.

A "$C_1$-$C_6$ alkoxy group" in the definitions of substituent group α, substituent group β, and substituent group γ refers to a group in which an aforementioned "$C_1$-$C_6$ alkyl group" is bonded to an oxygen atom. Examples include a methoxy group, an ethoxy group, a propoxy group, an isopropoxy group, a butoxy group, an isobutoxy group, a sec-butoxy group, a tert-butoxy group, a pentyloxy group, an isopentyloxy group, a 2-methylbutoxy group, a neopentyloxy group, a 1-ethylpropoxy group, a hexyloxy group, a 4-methylpentyloxy group, a 3-methylpentyloxy group, a 2-methylpentyloxy group, a 1-methylpentyloxy group, a 3,3-dimethylbutoxy group, a 2,2-dimethylbutoxy group, a 1,1-dimethylbutoxy group, a 1,2-dimethylbutoxy group, a 1,3-dimethylbutoxy group, a 2,3-dimethylbutoxy group, and a 2-ethylbutoxy group. The $C_1$-$C_6$ alkoxy group is preferably a methoxy group.

A "$C_1$-$C_6$ alkoxycarbonyl group" in the definition of $R^3$ refers to a group in which an aforementioned "$C_1$-$C_6$ alkoxy group" is bonded to a carbonyl group. Examples include a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, an isopentyloxycarbonyl group, a 2-methylbutoxycarbonyl group, a neopentyloxycarbonyl group, a 1-ethylpropoxycarbonyl group, a hexyloxycarbonyl group, a 4-methylpentyloxycarbonyl group, a 3-methylpentyloxycarbonyl group, a 2-methylpentyloxycarbonyl group, a 1-methylpentyloxycarbonyl group, a 3,3-dimethylbutoxycarbonyl group, a 2,2-dimethylbutoxycarbonyl group, a 1,1-dimethylbutoxycarbonyl group, a 1,2-dimethylbutoxycarbonyl group, a 1,3-dimethylbutoxycarbonyl group, a 2,3-dimethylbutoxycarbonyl group, and a 2-ethylbutoxycarbonyl group. The $C_1$-$C_6$ alkoxycarbonyl group is preferably a tert-butoxycarbonyl group.

A "$C_3$-$C_7$ cycloalkyl group" in the definitions of substituent group α, substituent group β, and substituent group γ refers to a cycloalkyl group having 3 to 7 carbon atoms. Examples include a cyclopropyl group, a cyclobutyl group, a cyclopentyl group, a cyclohexyl group, and a cycloheptyl group. The $C_3$-$C_7$ cycloalkyl group is preferably a cyclohexyl group.

A "4- to 7-membered heterocycloalkyl group" in the definition of substituent group α refers to a monocyclic non-aromatic heterocyclic group composed of a saturated, partially unsaturated, or unsaturated 4- to 7-membered ring containing 1 or 2 atoms selected from the group consisting of a nitrogen atom, an oxygen atom, and a sulfur atom. Examples include a tetrahydrofuranyl group, a tetrahydropyranyl group, a dioxolanyl group, a dioxanyl group, a dioxepanyl group, a pyrrolidinyl group, a piperidyl group, an azepanyl group, a dihydropyrrolyl group, a dihydropyridyl group, a tetrahydropyridyl group, a piperazinyl group, a morpholinyl group, a dihydrooxazolyl group, and a dihydrothiazolyl group. The 4- to 7-membered heterocycloalkyl group is preferably a morpholinyl group or a piperidinyl group.

A "monocyclic aromatic heterocyclic group" in the definitions of $Q^1$, $Q^2$, and $Q^3$ refers to a 5- to 7-membered monocyclic aromatic heterocyclic group containing 1 or 2 atoms selected from the group consisting of a nitrogen atom, an oxygen atom, and a sulfur atom. Examples include a pyrrolyl group, a pyridyl group, a thienyl group, a furyl group, a pyrimidinyl group, a pyranyl group, a pyridazinyl group, a pyrazinyl group, a pyrazolyl group, an imidazolyl group, a thiazolyl group, an isothiazolyl group, an oxazolyl group, and an isooxazolyl group. The monocyclic aromatic heterocyclic group in $Q^1$ is preferably a pyridyl group, a pyrimidinyl group, a pyrazinyl group, or a pyridazinyl group, more preferably a pyridyl group or a pyrimidinyl group. The monocyclic aromatic heterocyclic group in $Q^2$ and $Q^3$ is preferably a pyridyl group, a pyrimidinyl group, a pyrazinyl group, or a pyridazinyl group, more preferably a pyridyl group.

A "bicyclic aromatic heterocyclic group" in the definition of $Q^1$ refers to an aromatic heterocyclic group in which an aforementioned "monocyclic aromatic heterocyclic group" is fused with another cyclic group such as a benzene ring. Examples include a quinolyl group, an isoquinolyl group, a quinazolinyl group, a chromanyl group, an isochromanyl group, a benzofuranyl group, a dihydrobenzofuranyl group, a benzothiophenyl group, a dihydrobenzothiophenyl group, an indolyl group, an isoindolyl group, a quinoxalinyl group, a benzothiazolyl group, a tetrahydroquinolyl group, a tetrahydroisoquinolyl group, a benzoxazolyl group, a benzoxanyl group, an indolizinyl group, a thienopyridyl group, a dihydrothienopyridyl group, a furopyridyl group, a dihydrofuropyridyl group, a benzimidazolyl group, a benzothienyl group, an isobenzofuranyl group, and an indolinyl group. The bicyclic aromatic heterocyclic group is preferably a quinolyl group, an isoquinolyl group, or a quinazolinyl group.

An "aromatic hydrocarbon ring group" in the definitions of $Q^2$, $Q^3$, and $R^3$ refers to a monocyclic or bicyclic aromatic hydrocarbon ring group having 6 to 10 carbon atoms. Examples include a phenyl group, an indenyl group, a naphthyl group, an azulenyl group, a heptalenyl group, a cyclopentacyclooctenyl group, and a benzocyclooctenyl group. The aromatic hydrocarbon ring group is preferably a phenyl group.

In the compounds of the present invention, $R^1$ represents a group represented by $-Q^1$, $-Q^1-X-Q^2$, or $-Q^1-X-Q^2-Y-Q^3$.

In the case where $R^1$ represents a group represented by $-Q^1-X-Q^2$ or $-Q^1-X-Q^2-Y-Q^3$, $Q^1$ and $Q^2$ may each be a divalent substituent, which is however indicated herein in the form of a monovalent substituent.

In the case where $R^1$ represents a group represented by $-Q^1-X-Q^2$ or $-Q^1-X-Q^2-Y-Q^3$, the substitution position of the group $-X-Q^2$ or the group $-X-Q^2-Y-Q^3$ on $Q^1$ is explained hereinafter.

In the case where $Q^1$ is a 5-membered ring and the position of an atom bonded to X is defined as the 1-position, the substitution position of the group $-X-Q^2$ or the group $-X-Q^2-Y-Q^3$ is preferably the 3- or 4-position.

In the case where $Q^1$ is a 6-membered ring and the position of an atom bonded to X is defined as the 1-position, the substitution position of the group $-X-Q^2$ or the group $-X-Q^2-Y-Q^3$ is preferably the 3- or 4-position.

In the case where $Q^1$ is a 7-membered ring and the position of an atom bonded to X is defined as the 1-position, the substitution position of the group $-X-Q^2$ or the group $-X-Q^2-Y-Q^3$ is preferably the 4- or 5-position.

In the case where $Q^1$ is, for example, a pyridyl group, the substitution position of the group $-X-Q^2$ or the group $-X-Q^2-Y-Q^3$ is preferably a substitution position as described below.

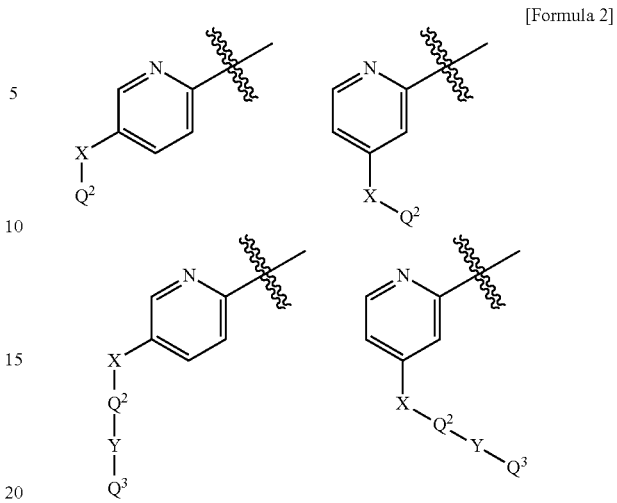

[Formula 2]

In the case where $Q^1$ is, for example, a pyrimidinyl group, the substitution position of the group $-X-Q^2$ or the group $-X-Q^2-Y-Q^3$ is preferably a substitution position as described below.

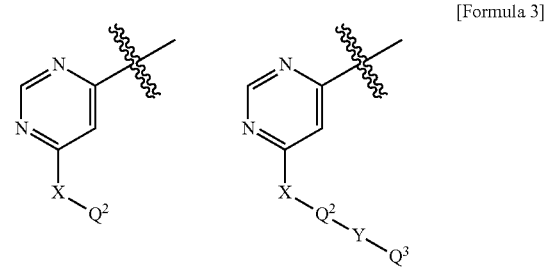

[Formula 3]

$Q^1$ in the present invention is preferably a pyridyl group, a pyrimidinyl group, a pyrazinyl group, a pyridazinyl group, a quinolyl group, an isoquinolyl group, or a quinazolinyl group which may have 1 or 2 substituents independently selected from substituent group α, more preferably a pyridyl group or a pyrimidinyl group which may have 1 or 2 substituents independently selected from substituent group α.

The substituent group α in the present invention is preferably the group consisting of a fluorine atom, a chlorine atom, a bromine atom, a methyl group, a methoxy group, a morpholinyl group, and a piperidinyl group. In the case where $R^1$ represents a group represented by $-Q^1$, the substituent group α is preferably the group consisting of a morpholinyl group and a piperidinyl group. In the case where $R^1$ represents a group represented by $-Q^1-X-Q^2$ or $-Q^1-X-Q^2-Y-Q^3$, the substituent group α is preferably the group consisting of a fluorine atom, a chlorine atom, a methyl group, and a methoxy group.

X in the present invention preferably represents a single bond, $-(CH_2)_n-$, $-CH=CH-$, $-CONH-$, $-NHCO-$, $-CONHCH_2-$, $-NHCOCH_2-$, $-CH_2NHCO-$, $-CH_2CONH-$, $-SO_2NH-$, $-CH_2OCH_2-$, or $-NHCH_2CH_2-$ and is more preferably $-CH_2-$, $-CH_2CH_2-$, $-CH=CH-$, $-CONH-$, $-CONHCH_2-$, $-CH_2OCH_2-$, or $-NHCH_2CH_2-$. In this context, a bond shown on the left side in each group refers to being bonded to the aforementioned $Q^1$.

n in the present invention is preferably 1 or 2.

Q² in the present invention is preferably a phenyl group, a pyridyl group, a pyrimidinyl group, a pyrazinyl group, or a pyridazinyl group which may have 1 or 2 substituents independently selected from substituent group β, more preferably a phenyl group or a pyridyl group which may have 1 or 2 substituents independently selected from substituent group β.

The substituent group β in the present invention is preferably the group consisting of a fluorine atom, a chlorine atom, a bromine atom, a methyl group, an ethyl group, a propyl group, an isopropyl group, a butyl group, an isobutyl group, a sec-butyl group, a tert-butyl group, a trifluoromethyl group, a cyclohexyl group, and a cyano group, more preferably the group consisting of a chlorine atom, a bromine atom, a trifluoromethyl group, a tert-butyl group, and a cyclohexyl group.

Y in the present invention is preferably a single bond, —O—, —(CH₂)ₙ—, or —O—(CH₂)ₙ—, more preferably a single bond or —O—. In this context, a bond shown on the left side in each group refers to being bonded to the aforementioned Q².

Q³ in the present invention is preferably a phenyl group, a pyridyl group, a pyrimidinyl group, a pyrazinyl group, or a pyridazinyl group which may have 1 or 2 substituents independently selected from substituent group γ, more preferably a phenyl group or a pyridyl group which may have 1 or 2 substituents independently selected from substituent group γ.

The substituent group γ in the present invention is preferably the group consisting of a fluorine atom, a chlorine atom, a bromine atom, a methyl group, an ethyl group, a propyl group, an isopropyl group, a trifluoromethyl group, and a cyano group, more preferably the group consisting of a chlorine atom, a bromine atom, a trifluoromethyl group, and a cyano group.

m in the present invention is preferably 1 or 2.

In the compounds of the present invention, R² is preferably a hydrogen atom or a methyl group.

In the compounds of the present invention, R³ is preferably a hydrogen atom, a methoxycarbonyl group, an ethoxycarbonyl group, a propoxycarbonyl group, a tert-butoxycarbonyl group, a carboxy group, a phenyl group, or a pyridyl group, more preferably a hydrogen atom.

The compound of the present invention is preferably one selected from the following compounds or pharmacologically acceptable salts thereof:

6-(4-acetamido-5-oxo-2,5-dihydro-1H-pyrazol-1-yl)-N-(4-cyclohexylphenyl)nicotinamide,
6-(4-acetamido-5-oxo-2,5-dihydro-1H-pyrazol-1-yl)-N-(4-tert-butylphenyl)nicotinamide,
6-(4-acetamido-5-oxo-2,5-dihydro-1H-pyrazol-1-yl)-N-(3-tert-butylphenyl)nicotinamide,
6-(4-acetamido-5-oxo-2,5-dihydro-1H-pyrazol-1-yl)-N-[4-(trifluoromethyl)phenyl]nicotinamide,
6-(4-acetamido-5-oxo-2,5-dihydro-1H-pyrazol-1-yl)-N-(4-chlorophenyl)nicotinamide,
N-[2-(6-morpholin-4-ylpyrimidin-4-yl)-3-oxo-2,3-dihydro-1H-pyrazol-4-yl]acetamide,
N-[3-oxo-2-(6-piperidin-1-ylpyrimidin-4-yl)-2,3-dihydro-1H-pyrazol-4-yl]acetamide,
N-(2-{5-[(benzyloxy)methyl]pyridin-2-yl}-3-oxo-2,3-dihydro-1H-pyrazol-4-yl)acetamide,
N-(3-oxo-2-{6-[(2-phenylethyl)amino]pyrimidin-4-yl}-2,3-dihydro-1H-pyrazol-4-yl)acetamide,
N-(2-{4-[(benzyloxy)methyl]pyridin-2-yl}-3-oxo-2,3-dihydro-1H-pyrazol-4-yl)acetamide,
6-(4-acetamido-5-oxo-2,5-dihydro-1H-pyrazol-1-yl)-N-(biphenyl-3-ylmethyl)nicotinamide,
6-(4-acetamido-5-oxo-2,5-dihydro-1H-pyrazol-1-yl)-N-[(2'-cyanobiphenyl-4-ylmethyl)]nicotinamide,
N-[2-(5-{[(2'-cyanobiphenyl-4-yl)methoxy]methyl}pyridin-2-yl)-3-oxo-2,3-dihydro-1H-pyrazol-4-yl]acetamide,
N-(2-{5-[(biphenyl-4-ylmethoxy)methyl]pyridin-2-yl}-3-oxo-2,3-dihydro-1H-pyrazol-4-yl)acetamide,
N-(2-{5-[(biphenyl-3-ylmethoxy)methyl]pyridin-2-yl}-3-oxo-2,3-dihydro-1H-pyrazol-4-yl)acetamide,
6-(4-acetamido-3-methyl-5-oxo-2,5-dihydro-1H-pyrazol-1-yl)-N-[4-(trifluoromethyl)phenyl]nicotinamide,
6-(4-acetamido-3-methyl-5-oxo-2,5-dihydro-1H-pyrazol-1-yl)-N-(4-chlorophenyl)nicotinamide,
6-(4-acetamido-3-methyl-5-oxo-2,5-dihydro-1H-pyrazol-1-yl)-N-(4-bromophenyl)nicotinamide,
6-(4-acetamido-3-methyl-5-oxo-2,5-dihydro-1H-pyrazol-1-yl)-N-(4-tert-butylphenyl)nicotinamide,
6-(4-acetamido-3-methyl-5-oxo-2,5-dihydro-1H-pyrazol-1-yl)-N-(6-phenylpyridin-3-yl)nicotinamide,
N-[2-(5-{[(2'-cyanobiphenyl-4-yl)methoxy]methyl}pyridin-2-yl)-5-methyl-3-oxo-2,3-dihydro-1H-pyrazol-4-yl]acetamide,
tert-butyl 4-[(5-methyl-3-oxo-2-{5-[(6-phenylpyridyl-3-yl)carbamoyl]pyridin-2-yl}-2,3-dihydro-1H-pyrazol-4-yl)amino]-4-oxobutanoate,
4-[(5-methyl-3-oxo-2-{5-[(6-phenylpyridyl-3-yl)carbamoyl]pyridin-2-yl}-2,3-dihydro-1H-pyrazol-4-yl)amino]-4-oxobutanoic acid,
N-{5-methyl-3-oxo-2-[5-({[4-(trifluoromethyl)benzyl]oxy}methyl)pyridin-2-yl]-2,3-dihydro-1H-pyrazol-4-yl}acetamide,
N-(5-methyl-3-oxo-2-{5-[4-(trifluoromethyl)benzyl]pyridin-2-yl}-2,3-dihydro-1H-pyrazol-4-yl)acetamide,
N-[5-methyl-3-oxo-2-(5-{2-[4-(trifluoromethyl)phenyl]ethyl}pyridin-2-yl)-2,3-dihydro-1H-pyrazol-4-yl]acetamide, and
N-[5-methyl-3-oxo-2-(5-{(E)-2-[4-(trifluoromethyl)phenyl]ethenyl}pyridin-2-yl)-2,3-dihydro-1H-pyrazol-4-yl]acetamide.

The compound of the present invention is more preferably one selected from the following compounds or pharmacologically acceptable salts thereof:

6-(4-acetamido-5-oxo-2,5-dihydro-1H-pyrazol-1-yl)-N-(4-cyclohexylphenyl)nicotinamide,
6-(4-acetamido-5-oxo-2,5-dihydro-1H-pyrazol-1-yl)-N-(4-tert-butylphenyl)nicotinamide,
6-(4-acetamido-5-oxo-2,5-dihydro-1H-pyrazol-1-yl)-N-(3-tert-butylphenyl)nicotinamide,
6-(4-acetamido-5-oxo-2,5-dihydro-1H-pyrazol-1-yl)-N-[4-(trifluoromethyl)phenyl]nicotinamide,
6-(4-acetamido-5-oxo-2,5-dihydro-1H-pyrazol-1-yl)-N-(4-chlorophenyl)nicotinamide,
N-[2-(6-morpholin-4-ylpyrimidin-4-yl)-3-oxo-2,3-dihydro-1H-pyrazol-4-yl]acetamide,
N-[3-oxo-2-(6-piperidin-1-ylpyrimidin-4-yl)-2,3-dihydro-1H-pyrazol-4-yl]acetamide,
N-(2-{5-[(benzyloxy)methyl]pyridin-2-yl}-3-oxo-2,3-dihydro-1H-pyrazol-4-yl)acetamide,
N-(2-{4-[(benzyloxy)methyl]pyridin-2-yl}-3-oxo-2,3-dihydro-1H-pyrazol-4-yl)acetamide,
6-(4-acetamido-5-oxo-2,5-dihydro-1H-pyrazol-1-yl)-N-(biphenyl-3-ylmethyl)nicotinamide,
N-[2-(5-{[(2'-cyanobiphenyl-4-yl)methoxy]methyl}pyridin-2-yl)-3-oxo-2,3-dihydro-1H-pyrazol-4-yl]acetamide,
N-(2-{5-[(biphenyl-4-ylmethoxy)methyl]pyridin-2-yl}-3-oxo-2,3-dihydro-1H-pyrazol-4-yl)acetamide,
N-(2-{5-[(biphenyl-3-ylmethoxy)methyl]pyridin-2-yl}-3-oxo-2,3-dihydro-1H-pyrazol-4-yl)acetamide, 6-(4-acetamido-3-methyl-5-oxo-2,5-dihydro-1H-pyrazol-1-yl)-N-(4-tert-butylphenyl)nicotinamide, N-[2-(5-{[(2'-cyanobiphenyl-4-yl)methoxy]methyl}pyridin-2-yl)-5-methyl-3-oxo-2,3-dihydro-1H-pyrazol-4-yl]acetamide, N-{5-methyl-3-oxo-2-[5-({[4-(trifluoromethyl)benzyl]oxy}methyl)pyridin-2-yl]-2,3-dihydro-1H-pyrazol-4-yl}acetamide, N-(5-methyl-3-oxo-2-{5-[4-(trifluoromethyl)benzyl]pyridin-2-yl}-2,3-dihydro-1H-pyrazol-4-yl)acetamide, and N-[5-methyl-3-oxo-2-(5-{2-[4-(trifluoromethyl)phenyl]ethyl}pyridin-2-yl)-2,3-dihydro-1H-pyrazol-4-yl]acetamide.

In the compounds of the present invention, geometrical isomers or tautomers may be present depending on the types of substituents. The 3-pyrazolone derivative represented by the general formula (1) of the present invention may be a tautomeric pyrazol-3-ol derivative (1a).

[Formula 4]

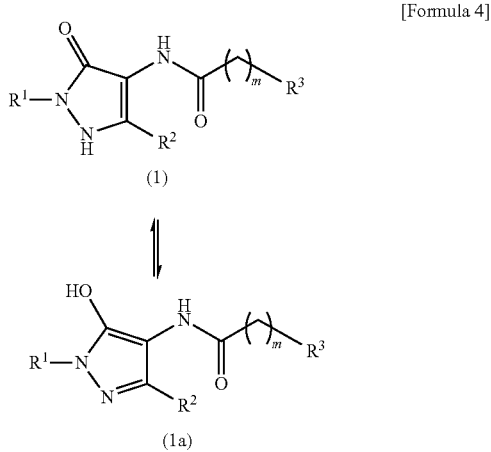

Further, in the case where the compounds of the present invention have an asymmetric carbon atom, optical isomers may be present. These separated isomers (e.g., enantiomers or diastereomers) and mixtures thereof (e.g., racemates or diastereomeric mixtures) are included in the present invention. Further, labeled compounds, namely compounds in which one or more atoms of compounds of the present invention have been substituted with a corresponding radioactive isotope or non-radioactive isotope in an arbitrary ratio, are also included in the present invention.

In the case where the compound of the present invention has a basic group such as an amino group, a pharmacologically acceptable acid addition salt can be formed, if desired. Examples of such acid addition salts include: hydrohalic acid salts such as hydrofluorides, hydrochlorides, hydrobromides, and hydroiodides; inorganic acid salts such as nitrates, perchlorates, sulfates, and phosphates; lower alkanesulfonates such as methanesulfonates, trifluoromethanesulfonates, and ethanesulfonates; aryl sulfonates such as benzenesulfonates and p-toluenesulfonates; organic acid salts such as formates, acetates, trifluoroacetates, malates, fumarates, succinates, citrates, tartrates, oxalates, and maleates; and amino acid salts such as ornithinates, glutamates, and aspartates, and hydrohalic acid salts and organic acid salts are preferred.

In the case where the compound of the present invention has an acidic group such as a carboxy group, generally a pharmacologically acceptable base addition salt can be formed. Examples of such base addition salts include: alkali metal salts such as sodium salts, potassium salts, and lithium salts; alkaline earth metal salts such as calcium salts and magnesium salts; inorganic salts such as ammonium salts; and organic amine salts such as dibenzylamine salts, morpholine salts, phenylglycine alkyl ester salts, ethylenediamine salts, N-methylglucamine salts, diethylamine salts, triethylamine salts, cyclohexylamine salts, dicyclohexylamine salts, N,N'-dibenzylethylenediamine salts, diethanolamine salts, N-benzyl-N-(2-phenylethoxy)amine salts, piperazine salts, tetramethylammonium salts, and tris(hydroxymethyl)aminomethane salts.

The compounds of the present invention may also be present as a non-solvate or a solvate. Although there are no particular limitations on the solvate provided it is pharmacologically acceptable, preferred specific examples include hydrates and ethanolates. Further, in the case where a nitrogen atom is present in a compound represented by the general formula (1), it may be in the form of an N-oxide, and these solvates and N-oxide forms are also included within the scope of the present invention.

Although the compounds of the present invention can be present in the form of various isomers including geometrical isomers such as a cis form or trans form, tautomers, or optical isomers such as a d form or l form depending on the types of substituents and combinations thereof, the compounds of the present invention also include all the isomers and mixtures of the isomers in any ratio thereof, unless otherwise specifically limited.

Further, the compounds of the present invention can contain a non-natural ratio of isotopes in one or more atoms constituting such compounds. Examples of the isotopes include deuterium ($^{2}H$; D), tritium ($^{3}H$; T), iodine-125 ($^{125}I$) and carbon-14 ($^{14}C$). Further, the compounds of the present invention can be radiolabeled with, for example, radioisotopes such as tritium ($^{3}H$), iodine-125 ($^{125}I$), or carbon-14 ($^{14}C$). A radiolabeled compound is useful as a therapeutic or prophylactic agent, a research reagent (e.g., an assay reagent), and a diagnostic agent (e.g., an in vivo diagnostic imaging agent). The compounds of the present invention containing all ratios of radioactive or non-radioactive isotopes are included within the scope of the present invention.

The compounds of the present invention can also be produced by applying various known synthesis methods depending on the basic skeleton thereof or types of substituents. In so doing, depending on the types of functional groups, it is possible to protect this functional group with a suitable protecting group at stages from a raw material to an intermediate, or replace it with a group that can be easily converted to this functional group. Examples of such functional groups include an amino group, a hydroxy group, and a carboxy group. Examples of their protecting groups include those described in, for example, Protective Groups in Organic Synthesis, 3rd ed., Greene, T. W., Wuts, P. G. M., John Wiley & Sons, Inc., New York, 1999, and these protecting groups can be appropriately selected and used depending on the reaction conditions thereof. According to such methods, a desired compound can be obtained by introducing this protecting group and carrying out the reaction followed by removing the protecting group as necessary, or converting it to a desired group. The resulting compounds of the present invention can be identified, and their composition or purity can be analyzed, by standard analytical technologies such as elementary analysis, NMR, mass spectroscopy, or IR analysis.

Raw materials and reagents used to produce the compounds of the present invention can be purchased from commercial suppliers, or can be synthesized according to methods described in the literature.

In the present invention, examples of anemia include nephrogenic anemia, anemia of prematurity, anemia incidental to chronic diseases, anemia incidental to cancer chemotherapy, cancerous anemia, inflammation-associated anemia, and anemia incidental to congestive heart failure. Examples of the anemia incidental to chronic diseases include anemia incidental to chronic kidney diseases, and examples of the chronic kidney diseases include chronic renal failure. Further, the patient to whom the compound of the present invention is administered can be a patient who does or does not receive dialysis.

Effects of Invention

The compounds of the present invention or pharmacologically acceptable salts thereof demonstrate a superior EPO production-enhancing activity in an assay system using Hep3B cells, and have superior safety. Specifically, EPO production can be enhanced by administering a pharmaceutical composition containing a compound of the present invention or a pharmacologically acceptable salt thereof to a mammal (such as a human, cow, horse, or pig) or a bird (such as a chicken). Thus, a pharmaceutical composition containing a compound of the present invention or a pharmacologically acceptable salt thereof can be used for the prophylaxis and/or treatment of, for example, diseases caused by decreased EPO, or diseases or pathological conditions in which EPO is decreased such as ischemic cerebrovascular disease, or for autologous transfusion in patients scheduled to undergo surgery. Examples of diseases caused by decreased EPO include anemia, and particularly nephrogenic anemia (dialysis stage, conservation stage), anemia of prematurity, anemia incidental to chronic diseases, anemia incidental to cancer chemotherapy, cancerous anemia, inflammation-associated anemia, and anemia incidental to congestive heart failure.

DESCRIPTION OF EMBODIMENTS

The following provides examples of representative methods for producing the compounds of the present invention. Furthermore, the production methods of the present invention are not limited to the examples shown below.

(Step 1)

Step 1 is a step for producing a compound having the general formula (1) from a compound having the general formula (2) to be subsequently described.

[Formula 5]

Step 1

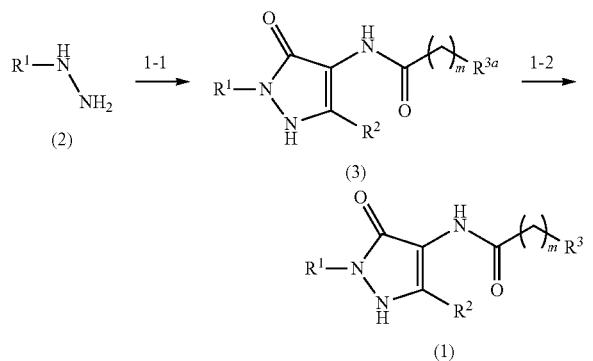

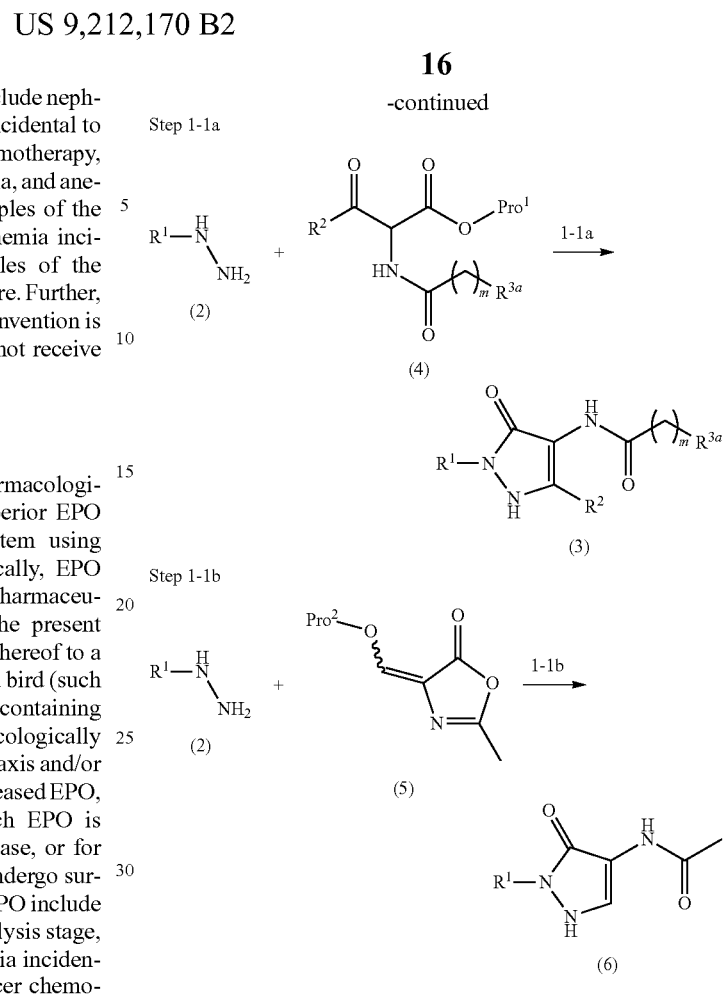

In the above formulae, $R^1$ to $R^3$ and m have the same meanings as previously defined; $R^{3a}$ represents the aforementioned $R^3$ or a group that can be converted to $R^3$; and $Pro^1$ and $Pro^2$ represent protecting groups of the respective functional groups selected from known protecting groups (e.g., T. W. Greene, P. G. M. Wuts, Protective Groups in Organic Synthesis, Third Edition, John Wiley & Sons Inc., 1999). Although there are no particular limitations on $Pro^1$ and $Pro^2$ provided they are stable during the reaction and do not inhibit the reaction, preferably $Pro^1$ represents a methyl group or an ethyl group and Pro represents an ethyl group.

The following provides a detailed description of each step.

(Step 1-1)

Step 1-1 is a step for producing a compound having the general formula (3) from a compound having the general formula (2) to be subsequently described. Examples of essential reactions include:

Step 1-1a: condensation reaction with a compound having the general formula (4) to be subsequently described; or Step 1-1b: condensation reaction with a compound having the general formula (5).

Step 1-2: reaction for converting $R^{3a}$ to $R^3$ can be added, as necessary.

(Step 1-1a)

This step involves the condensation reaction of the compound having the general formula (2) to be subsequently described with the compound having the general formula (4) to be subsequently described and is carried out in the presence of a base and in the presence or absence of an acid in an inert solvent.

Although there are no particular limitations on the solvent used provided it does not inhibit the reaction and dissolves the starting material to a certain degree, preferred examples include: aromatic hydrocarbons such as benzene, toluene, and xylene; halogenated hydrocarbons such as dichloromethane and chloroform; esters such as ethyl acetate and propyl acetate; ethers such as diethyl ether, tetrahydrofuran, 1,4-dioxane, and 1,2-dimethoxyethane; alcohols such as methanol, ethanol, and tert-butanol; nitriles such as acetonitrile; amides such as formamide and N,N-dimethylformamide; sulfoxides such as dimethyl sulfoxide; a mixture of multiple organic solvents in an arbitrary ratio; and a mixture thereof with water in an arbitrary ratio.

Although there are no particular limitations on the base used provided it is used as a base in conventional reactions, preferred examples include: organic bases such as triethylamine, N,N-diisopropylethylamine, N-methylmorpholine, lutidine, and pyridine; alkali metal carbonates such as sodium carbonate and potassium carbonate; alkaline earth metal carbonates such as calcium carbonate; alkali metal hydrogencarbonates such as potassium hydrogencarbonate; alkaline earth metal hydrogencarbonates such as calcium hydrogencarbonate; alkali metal hydroxides such as sodium hydroxide; alkaline earth metal hydroxides such as calcium hydroxide; and alkali metal phosphates such as tripotassium phosphate.

Although there are no particular limitations on the acid used provided it is used as an acid in conventional reactions, examples include: inorganic acids such as hydrochloric acid and sulfuric acid; Lewis acids such as boron trifluoride, boron trichloride, boron tribromide, and iodotrimethylsilane; and organic acids such as trifluoroacetic acid and acetic acid.

Varying according to the raw material compounds, reagents and the like, the reaction temperature is normally −10° C. to 150° C., preferably 20° C. to 100° C.

Varying according to the raw material compounds, reagents and the like, the reaction time is normally 5 minutes to 48 hours, preferably 10 minutes to 12 hours.

Following completion of the reaction, the desired compound of the present reaction can be obtained as a solid by, for example, concentrating the reaction mixture and adding an organic solvent such as diisopropyl ether. On the other hand, in the case where a solid is unable to be obtained, the desired compound can be obtained by extracting an organic substance with an organic solvent such as ethyl acetate, drying the organic layer with a commonly used procedure and subsequently concentrating it under reduced pressure.

The resulting compound can be further purified if necessary using a conventional method, for example, recrystallization, reprecipitation, or silica gel column chromatography.
(Step 1-1b)

This step involves the condensation reaction of the compound having the general formula (2) to be subsequently described with the compound having the general formula (5) and is carried out in the presence of a base and in the presence or absence of an acid in an inert solvent.

Although there are no particular limitations on the solvent used provided it does not inhibit the reaction and dissolves the starting material to a certain degree, preferred examples include: aromatic hydrocarbons such as benzene, toluene, and xylene; halogenated hydrocarbons such as dichloromethane and chloroform; esters such as ethyl acetate and propyl acetate; ethers such as diethyl ether, tetrahydrofuran, 1,4-dioxane, and 1,2-dimethoxyethane; alcohols such as methanol, ethanol, and tert-butanol; nitriles such as acetonitrile; amides such as formamide and N,N-dimethylformamide; sulfoxides such as dimethyl sulfoxide; a mixture of multiple organic solvents in an arbitrary ratio; and a mixture thereof with water in an arbitrary ratio.

Although there are no particular limitations on the base used provided it is used as a base in conventional reactions, preferred examples include: organic bases such as triethylamine, N,N-diisopropylethylamine, N-methylmorpholine, lutidine, and pyridine; alkali metal carbonates such as sodium carbonate and potassium carbonate; alkaline earth metal carbonates such as calcium carbonate; alkali metal hydrogencarbonates such as potassium hydrogencarbonate; alkaline earth metal hydrogencarbonates such as calcium hydrogencarbonate; alkali metal hydroxides such as sodium hydroxide; alkaline earth metal hydroxides such as calcium hydroxide; and alkali metal phosphates such as tripotassium phosphate.

Although there are no particular limitations on the acid used provided it is used as an acid in conventional reactions, examples include: inorganic acids such as hydrochloric acid and sulfuric acid; Lewis acids such as boron trifluoride, boron trichloride, boron tribromide, and iodotrimethylsilane; and organic acids such as trifluoroacetic acid and acetic acid.

Varying according to the raw material compounds, reagents and the like, the reaction temperature is normally −10° C. to 150° C., preferably 20° C. to 100° C.

Varying according to the raw material compounds, reagents and the like, the reaction time is normally 5 minutes to 48 hours, preferably 10 minutes to 12 hours.

Following completion of the reaction, the desired compound of the present reaction can be obtained as a solid by, for example, concentrating the reaction mixture and adding an organic solvent such as diisopropyl ether. On the other hand, in the case where a solid is unable to be obtained, the desired compound can be obtained by extracting an organic substance with an organic solvent such as ethyl acetate, drying the organic layer with a commonly used procedure and subsequently concentrating it under reduced pressure.

The resulting compound can be further purified if necessary using a conventional method, for example, recrystallization, reprecipitation, or silica gel column chromatography.
(Step 1-2)

This step involves a reaction for converting $R^{3a}$ to a carboxy group in the case where $R^{3a}$ is an alkoxycarbonyl group.
(Step 1-2a)

This step is a method for converting $R^{3a}$ to a carboxy group using a suitable base in an inert solvent.

Although there are no particular limitations on the solvent used provided it does not inhibit the reaction and dissolves the starting material to a certain degree, preferred examples include: aromatic hydrocarbons such as benzene, toluene, and xylene; halogenated hydrocarbons such as dichloromethane and chloroform; ethers such as diethyl ether, tetrahydrofuran, 1,4-dioxane, and 1,2-dimethoxyethane; alcohols such as methanol, ethanol, and tert-butanol; esters such as ethyl acetate and propyl acetate; nitriles such as acetonitrile; amides such as formamide and N,N-dimethylformamide; sulfoxides such as dimethyl sulfoxide; a mixture of multiple organic solvents in an arbitrary ratio; and in addition, a mixture thereof with water in an arbitrary ratio.

Although there are no particular limitations on the base used provided it is used as a base in conventional reactions, examples include: organic bases such as triethylamine; alkali metal carbonates such as sodium carbonate and potassium carbonate; alkaline earth metal carbonates such as calcium carbonate; alkali metal hydrogencarbonates such as potassium hydrogencarbonate; alkaline earth metal hydrogencarbonates such as calcium hydrogencarbonate; alkali metal hydroxides such as sodium hydroxide and potassium hydroxide; alkaline earth metal hydroxides such as calcium hydroxide; and alkali metal phosphates such as tripotassium phosphate.

Varying according to the raw material compounds, reagents and the like, the reaction temperature is normally −10° C. to 150° C., preferably 10° C. to 90° C.

Varying according to the raw material compounds, reagents and the like, the reaction time is normally 1 minute to 24 hours, preferably 10 minutes to 6 hours.

Following completion of the reaction, the desired compound can be obtained as a solid by distilling off the organic solvent, adding water and then adding an acid. On the other hand, in the case where a solid is unable to be obtained by adding an acid, the desired compound can be obtained by extracting an organic substance with an organic solvent such as ethyl acetate followed by concentrating the organic layer after having dried it with a commonly used procedure, or concentrating it under reduced pressure after having added an acid.

The resulting compound can be further purified if necessary using a conventional method, for example, recrystallization, reprecipitation, or silica gel column chromatography.

(Step 1-2b)

This step is a step for converting $R^{3a}$ to a carboxy group using a suitable acid in an inert solvent.

Although there are no particular limitations on the solvent used provided it does not inhibit the reaction and dissolves the starting material to a certain degree, preferred examples include: aromatic hydrocarbons such as benzene, toluene, and xylene; halogenated hydrocarbons such as dichloromethane and chloroform; esters such as ethyl acetate and propyl acetate; ethers such as diethyl ether, tetrahydrofuran, 1,4-dioxane, and 1,2-dimethoxyethane; alcohols such as methanol and ethanol; nitriles such as acetonitrile; amides such as formamide and N,N-dimethylformamide; sulfoxides such as dimethyl sulfoxide; a mixture of multiple organic solvents in an arbitrary ratio; and in addition, a mixture thereof with water in an arbitrary ratio.

Although there are no particular limitations on the acid used provided it is used as an acid in conventional reactions, examples include: inorganic acids such as hydrochloric acid and sulfuric acid; Lewis acids such as boron trifluoride, boron trichloride, boron tribromide, and iodotrimethylsilane; and organic acids such as trifluoroacetic acid.

Varying according to the raw material compounds, reagents and the like, the reaction temperature is normally −100° C. to 150° C., preferably −78° C. to 100° C.

Varying according to the raw material compounds, reagents and the like, the reaction time is normally 5 minutes to 24 hours, preferably 10 minutes to 12 hours.

Following completion of the reaction, the desired compound can be obtained as a solid by distilling off the organic solvent, adding water and then adding a base. On the other hand, in the case where a solid is unable to be obtained by adding a base, the desired compound can be obtained by extracting an organic substance with an organic solvent such as ethyl acetate followed by concentrating the organic layer after having dried it with a commonly used procedure, or concentrating it under reduced pressure after having added a base.

The resulting compound can be further purified if necessary using a conventional method, for example, recrystallization, reprecipitation, or silica gel column chromatography.

(Step 2)

Step 2 is a step for producing the compound having the general formula (2) for use in Step 1.

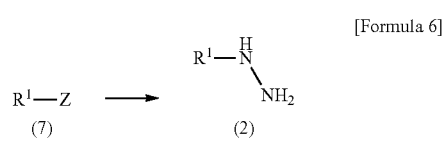

[Formula 6]

In the above formulae, $R^1$ has the same meaning as previously defined; and Z represents a halogen atom or a leaving group (—OW).

Although there are no particular limitations on W in the leaving group (—OW) provided it forms a known leaving group, preferred examples include substituted or unsubstituted alkylsulfonyl groups and arylsulfonyl groups, such as a trifluoromethanesulfonyl group.

The following provides a detailed description of each step.

(Step 2)

Step 2 is a step for producing the aforementioned compound having the general formula (2) from a compound having the general formula (7). Examples of essential reactions include:

condensation reaction of the compound having the general formula (7) with hydrazine hydrate or a hydrazine salt.

This step is carried out in the presence or absence of a base in an inert solvent.

Although there are no particular limitations on the solvent used provided it does not inhibit the reaction and dissolves the starting material to a certain degree, preferred examples include: aromatic hydrocarbons such as benzene, toluene, and xylene; halogenated hydrocarbons such as dichloromethane and chloroform; esters such as ethyl acetate and propyl acetate; ethers such as diethyl ether, tetrahydrofuran, 1,4-dioxane, and 1,2-dimethoxyethane; alcohols such as methanol, ethanol, and tert-butanol; nitriles such as acetonitrile; amides such as formamide and N,N-dimethylformamide; sulfoxides such as dimethyl sulfoxide; a mixture of multiple organic solvents in an arbitrary ratio; and a mixture thereof with water in an arbitrary ratio.

Although there are no particular limitations on the base used provided it is used as a base in conventional reactions, preferred examples include: organic bases such as triethylamine, N,N-diisopropylethylamine, N-methylmorpholine, lutidine, and pyridine; alkali metal carbonates such as sodium carbonate and potassium carbonate; alkaline earth metal carbonates such as calcium carbonate; alkali metal hydrogencarbonates such as potassium hydrogencarbonate; alkaline earth metal hydrogencarbonates such as calcium hydrogencarbonate; alkali metal hydroxides such as sodium hydroxide; alkaline earth metal hydroxides such as calcium hydroxide; and alkali metal phosphates such as tripotassium phosphate.

Varying according to the raw material compounds, reagents and the like, the reaction temperature is normally −10° C. to 200° C., preferably 20° C. to 150° C.

Varying according to the raw material compounds, reagents and the like, the reaction time is normally 5 minutes to 48 hours, preferably 10 minutes to 12 hours.

Following completion of the reaction, the desired compound of the present reaction can be obtained as a solid by, for example, concentrating the reaction mixture and adding an organic solvent such as diisopropyl ether. On the other hand, in the case where a solid is unable to be obtained, the desired compound can be obtained by extracting an organic substance with an organic solvent such as ethyl acetate, drying the organic layer with a commonly used procedure and subsequently concentrating it under reduced pressure.

The resulting compound can be further purified, if necessary, using a conventional method, for example, recrystallization, reprecipitation, or silica gel column chromatography.

(Step 3)

Step 3 is a step for producing the compound having the general formula (4) for use in Step 1.

[Formula 7]

Step 3

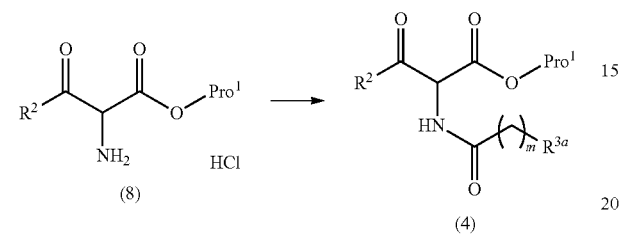

Step 3-a (followed by scheme showing compound (8) + HO-(CH2)m-R3a (9) → (4))

Step 3-b (scheme showing compound (8) + Cl-CO-(CH2)m-R3a (10) → (4))

Step 3-c (scheme showing compound (8) + Pro3-O-CO-O-CO-(CH2)m-R3a (11) → (4))

In the above formulae, $R^2$ and m have the same meanings as previously defined; $R^{3a}$ represents the aforementioned $R^3$ or a group that can be converted to $R^3$; and $Pro^1$ and $Pro^3$ represent protecting groups of the respective functional groups selected from known protecting groups (e.g., T. W. Greene, P. G. M. Wuts, Protective Groups in Organic Synthesis, Third Edition, John Wiley & Sons Inc., 1999). Although there are no particular limitations on $Pro^1$ and $Pro^3$ provided they are stable during the reaction and do not inhibit the reaction, preferably $Pro^1$ represents a methyl group or an ethyl group and $Pro^3$ represents an isobutyl group.

The following provides a detailed description of each step.

(Step 3)

Step 3 is a step for producing the aforementioned compound having the general formula (4) from a compound having the general formula (8). Examples of essential reactions include:

Step 3-a: condensation reaction of the compound having the general formula (8) with a carboxylic acid having the general formula (9);

Step 3-b: acylation reaction of the compound having the general formula (8) with an acid chloride having the general formula (10); or Step 3-c: acylation reaction of the compound having the general formula (8) with an active ester having the general formula (11).

(Step 3-a)

This step is a step for condensing the compound having the general formula (8) with a carboxylic acid having the general formula (9) and is carried out using a condensation agent in the presence or absence of a base in an inert solvent.

Although there are no particular limitations on the solvent used provided it does not inhibit the reaction and dissolves the starting material to a certain degree, preferred examples include: aromatic hydrocarbons such as benzene, toluene, and xylene; halogenated hydrocarbons such as dichloromethane and chloroform; esters such as ethyl acetate and propyl acetate; ethers such as diethyl ether, tetrahydrofuran, 1,4-dioxane, and 1,2-dimethoxyethane; alcohols such as methanol, ethanol, and tert-butanol; nitriles such as acetonitrile; amides such as formamide and N,N-dimethylformamide; sulfoxides such as dimethyl sulfoxide; a mixture of multiple organic solvents in an arbitrary ratio; and a mixture thereof with water in an arbitrary ratio.

Although there are no particular limitations on the base used provided it is used as a base in conventional reactions, preferred examples include: organic bases such as triethylamine, N,N-diisopropylethylamine, N-methylmorpholine, lutidine, and pyridine; alkali metal carbonates such as sodium carbonate and potassium carbonate; alkaline earth metal carbonates such as calcium carbonate; alkali metal hydrogencarbonates such as potassium hydrogencarbonate; alkaline earth metal hydrogencarbonates such as calcium hydrogencarbonate; alkali metal hydroxides such as sodium hydroxide; alkaline earth metal hydroxides such as calcium hydroxide; and alkali metal phosphates such as tripotassium phosphate.

Although there are no particular limitations on the condensation agent used provided it is used as a condensation agent that forms an amide bond (e.g., Shoichi Kusumoto et al., Experimental Science Course IV, Chemical Society of Japan, Maruzen Publishing, 1990; and Nobuo Izumiya et al., Peptide Synthesis Basics and Experimentation, Maruzen Publishing, 1985), preferred examples include O-benzotriazole-N,N,N',N'-tetramethyluronium hexafluorophosphate (HBTU), 2-(1H-benzotriazol-1-yl)-1,1,3,3-tetramethyluronium tetrafluoroborate (TBTU), 1-(3-dimethylaminopropyl)-3-ethylcarbodiimide hydrochloride (EDCI), 4-(2-{[(cyclohexylimino)methylene]amino}ethyl-4-methylmorpholin-4-ium para-toluenesulfonate (CMC), dicyclohexylcarbodiimide (DCC), 1,1'-carbonylbis(1H-imidazole) (CDI), (1H-benzotriazol-1-yloxy)(tripyrrolidin-1-yl)phosphonium hexafluorophosphate (PyBOP), bromo(tripyrrolidin-1-yl)phosphonium hexafluorophosphate (PyBrOP), 4-(4,6-dimethoxy-1,3,5-triazin-2-yl)-4-methylmorpholinium chloride (DMT-MM), and 2-chloro-4,6-dimethoxy-1,3,5-triazine (DMT). An additive such as 1-hydroxybenzotriazole (HOBT) or N,N-dimethylaminopyridine may also be added.

Varying according to the raw material compounds, reagents and the like, the reaction temperature is normally −10° C. to 150° C., preferably 0° C. to 100° C.

Varying according to the raw material compounds, reagents and the like, the reaction time is normally 5 minutes to 48 hours, preferably 10 minutes to 24 hours.

Following completion of the reaction, the desired compound of the present reaction can be obtained by, for example, concentrating the reaction mixture, adding an organic solvent such as ethyl acetate and washing with water followed by separating the organic layer containing the desired compound, drying with anhydrous sodium sulfate and the like, and distilling off the solvent.

The resulting compound can be further purified if necessary using a conventional method, for example, recrystallization, reprecipitation, or silica gel column chromatography.
(Step 3-b)

This step is a step for condensing the compound having the general formula (8) with an acid chloride having the general formula (10) and is carried out in the presence or an absence of a base in an inert solvent.

Although there are no particular limitations on the solvent used provided it does not inhibit the reaction and dissolves the starting material to a certain degree, preferred examples include: aromatic hydrocarbons such as benzene, toluene, and xylene; halogenated hydrocarbons such as dichloromethane and chloroform; esters such as ethyl acetate and propyl acetate; ethers such as diethyl ether, tetrahydrofuran, 1,4-dioxane, and 1,2-dimethoxyethane; nitriles such as acetonitrile; amides such as formamide and N,N-dimethylformamide; sulfoxides such as dimethyl sulfoxide; a mixture of multiple organic solvents in an arbitrary ratio; and a mixture thereof with water in an arbitrary ratio.

Although there are no particular limitations on the base used provided it is used as a base in conventional reactions, preferred examples include: organic bases such as triethylamine, N,N-diisopropylethylamine, N-methylmorpholine, lutidine, and pyridine; alkali metal carbonates such as sodium carbonate and potassium carbonate; alkaline earth metal carbonates such as calcium carbonate; alkali metal hydrogencarbonates such as potassium hydrogencarbonate; alkaline earth metal hydrogencarbonates such as calcium hydrogencarbonate; alkali metal hydroxides such as sodium hydroxide; alkaline earth metal hydroxides such as calcium hydroxide; and alkali metal phosphates such as tripotassium phosphate.

Varying according to the raw material compounds, reagents and the like, the reaction temperature is normally −80° C. to 150° C., preferably 0° C. to 80° C.

Varying according to the raw material compounds, reagents and the like, the reaction time is normally 5 minutes to 48 hours, preferably 10 minutes to 24 hours.

Following completion of the reaction, the desired compound of the present reaction can be obtained by, for example, concentrating the reaction mixture, adding an organic solvent such as ethyl acetate and washing with water followed by separating the organic layer containing the desired compound, drying with anhydrous sodium sulfate and the like, and distilling off the solvent.

The resulting compound can be further purified if necessary using a conventional method, for example, recrystallization, reprecipitation, or silica gel column chromatography.
(Step 3-c)

This step is a step for condensing the compound having the general formula (8) with an active ester having the general formula (11) and is carried out in the presence or absence of a base in an inert solvent.

Although there are no particular limitations on the solvent used provided it does not inhibit the reaction and dissolves the starting material to a certain degree, preferred examples include: aromatic hydrocarbons such as benzene, toluene, and xylene; halogenated hydrocarbons such as dichloromethane and chloroform; esters such as ethyl acetate and propyl acetate; ethers such as diethyl ether, tetrahydrofuran, 1,4-dioxane, and 1,2-dimethoxyethane; nitriles such as acetonitrile; amides such as formamide and N,N-dimethylformamide; sulfoxides such as dimethyl sulfoxide; a mixture of multiple organic solvents in an arbitrary ratio; and a mixture thereof with water in an arbitrary ratio.

Although there are no particular limitations on the base used provided it is used as a base in conventional reactions, preferred examples include: organic bases such as triethylamine, N,N-diisopropylethylamine, N-methylmorpholine, lutidine, and pyridine; alkali metal carbonates such as sodium carbonate and potassium carbonate; alkaline earth metal carbonates such as calcium carbonate; alkali metal hydrogencarbonates such as potassium hydrogencarbonate; alkaline earth metal hydrogencarbonates such as calcium hydrogencarbonate; alkali metal hydroxides such as sodium hydroxide; alkaline earth metal hydroxides such as calcium hydroxide; and alkali metal phosphates such as tripotassium phosphate.

Varying according to the raw material compounds, reagents and the like, the reaction temperature is normally −10° C. to 150° C., preferably 0° C. to 100° C.

Varying according to the raw material compounds, reagents and the like, the reaction time is normally 5 minutes to 48 hours, preferably 10 minutes to 24 hours.

Following completion of the reaction, the desired compound of the present reaction can be obtained by, for example, concentrating the reaction mixture, adding an organic solvent such as ethyl acetate and washing with water followed by separating the organic layer containing the desired compound, drying with anhydrous sodium sulfate and the like, and distilling off the solvent.

The resulting compound can be further purified if necessary using a conventional method, for example, recrystallization, reprecipitation, or silica gel column chromatography.

The reaction products obtained according to each of the aforementioned steps are isolated and purified as non-solvates, salts thereof or various types of solvates such as hydrates. Salts thereof can be produced according to a conventional method. Isolation or purification is carried out by applying conventional methods such as extraction, concentration, distillation, crystallization, filtration, recrystallization, or various types of chromatography.

Each type of isomer can be isolated in accordance with conventional methods by utilizing differences in physicochemical properties between isomers. For example, optical isomers can be separated by common optical resolution methods (e.g., fractional crystallization, chromatography, etc.). Further, optical isomers can also be produced from suitable optically active raw material compounds.

A formulation containing a compound of the present invention as an active ingredient is prepared using additives such as a carrier and an excipient used for conventional formulations. Administration of a compound of the present invention may be oral administration in the form of tablets, pills, capsules, granules, powders, liquids, or the like, or parenteral administration in the form of injections (e.g., intravenous injection and intramuscular injection), suppositories, transcutaneous agents, nasal agents, inhalants, or the like. Dosage and frequency of administration of a compound of the present invention are suitably determined on an individual basis in consideration of such factors as symptoms and age or gender of the recipient. The dosage is normally 0.001 to 100 mg/kg per administration for a human adult in the case of oral administration, and in the case of intravenous administration, the dosage is normally 0.0001 to 10 mg/kg per administration for a human adult. The frequency of administration is normally 1 to 6 times a day, or once a day to once in 7 days. It is also preferred that administration to a patient who receives dialysis should be carried out once before or after each dialysis (preferably before dialysis) that the patient receives.

Solid formulations for oral administration according to the present invention may be tablets, powders, granules, or the like. Such formulations are produced in accordance with a conventional method by mixing one or more active substances with an inert excipient, lubricant, disintegrant, or dissolution aid. The excipient may be, for example, lactose, mannitol, or glucose. The lubricant may be, for example, magnesium stearate. The disintegrant may be, for example, sodium carboxymethyl starch. The tablets or pills may be provided with a sugar coating, or a gastric or enteric coating as necessary.

Liquid formulations for oral administration may be pharmaceutically acceptable emulsions, liquids, suspensions, syrups, elixirs, or the like. Such formulations may contain commonly used inert solvents (e.g., purified water or ethanol), and may further contain solubilizers, wetting agents, suspending agents, sweeteners, corrigents, fragrances, or preservatives.

Injections for parenteral administration may be sterile aqueous or non-aqueous liquid formulations, suspensions or emulsions. Aqueous solvents for injections may be, for example, distilled water or physiological saline. Non-aqueous solvents for injections may be, for example, propylene glycol, polyethylene glycol, vegetable oils such as olive oil, alcohols such as ethanol, or Polysorbate 80 (Japanese Pharmacopoeia name). Such formulations may further contain isotonic agents, preservatives, wetting agents, emulsifiers, dispersants, stabilizers, or dissolution aids. These formulations may be sterilized, for example, by passing through a bacteria-retaining filter, incorporation of a bactericide, or irradiation. Further, it is also possible to use, as these formulations, compositions obtained by dissolving or suspending a sterile solid composition in sterile water or a solvent for injection prior to use.

EXAMPLES

Although the following provides examples and test examples to explain the present invention in more detail, the scope of the present invention is not limited thereto.

Example 1

6-(4-Acetamido-5-oxo-2,5-dihydro-1H-pyrazol-1-yl)-N-(4-cyclohexylphenyl)nicotinamide

[Formula 8]

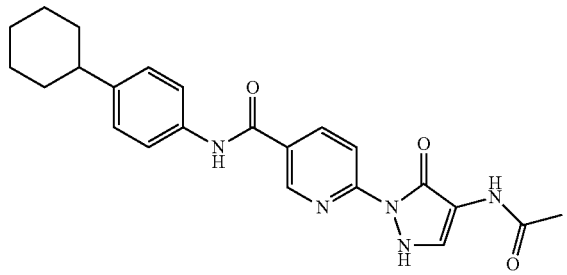

(1) 6-Chloro-N-(4-cyclohexylphenyl)nicotinamide

[Formula 9]

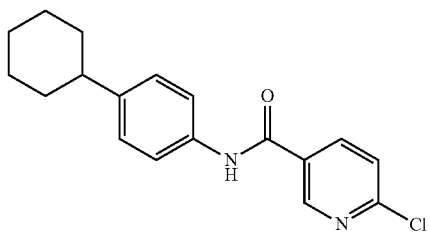

6-Chloronicotinoyl chloride (0.24 g) was dissolved in toluene (5 mL), and the solution was cooled to 0° C. 4-Cyclohexylaniline (0.47 g) was added thereto at 0° C., and the mixture was stirred at room temperature for 1 hour. Ethyl acetate was added thereto, and the organic layer was washed with a 1 N aqueous sodium hydroxide solution and water and dried over sodium sulfate. After concentration under reduced pressure, the obtained solid was collected by filtration and washed with diethyl ether. The solid was dried under reduced pressure to obtain the title compound (0.40 g) as a white solid (yield: 95%).

$^1$H-NMR (500 MHz, CDCl$_3$) δ: 8.85 (1H, d, J=2 Hz), 8.17 (1H, dd, J=8 Hz, 2 Hz), 7.68 (1H, brs), 7.52 (2H, d, J=9 Hz), 7.47 (1H, d, J=8 Hz), 7.24 (2H, d, J=9 Hz), 2.56-2.46 (1H, m), 1.92-1.80 (4H, m), 1.80-1.71 (1H, m), 1.46-1.36 (4H, m), 1.33-1.20 (1H, m).

(2) N-(4-Cyclohexylphenyl)-6-hydrazinonicotinamide

[Formula 10]

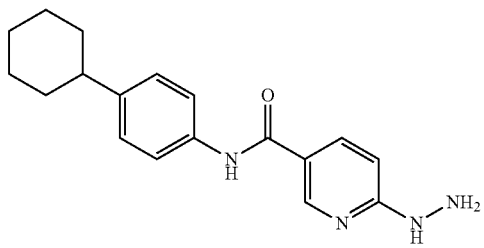

6-Chloro-N-(4-cyclohexylphenyl)nicotinamide (0.40 g) and hydrazine monohydrate (3 mL) were suspended in ethanol (6 mL), and the suspension was heated to reflux for 2 hours. The reaction solution was concentrated under reduced pressure, and the obtained solid was then collected by filtration and washed with an ethyl acetate-ethanol mixed solvent. The solid was dried under reduced pressure to obtain the title compound (0.39 g) as a white solid (yield: 99%).

$^1$H-NMR (500 MHz, DMSO-$d_6$) δ: 9.86 (1H, s), 8.62 (1H, d, J=2 Hz), 8.13 (1H, brs), 8.00 (1H, dd, J=9 Hz, 2 Hz), 7.62 (2H, d, J=8 Hz), 7.16 (1H, d, J=8 Hz), 6.75 (2H, d, J=9 Hz), 6.50 (2H, brs), 2.50-2.39 (1H, m), 1.84-1.74 (4H, m), 1.74-1.64 (1H, m), 1.43-1.30 (4H, m), 1.28-1.16 (1H, m).

(3) 6-(4-Acetamido-5-oxo-2,5-dihydro-1H-pyrazol-1-yl)-N-(4-cyclohexylphenyl)nicotinamide

[Formula 11]

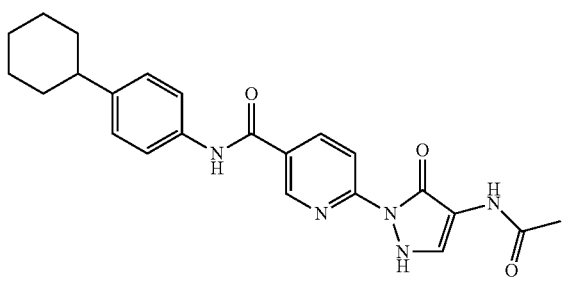

N-(4-Cyclohexylphenyl)-6-hydrazinonicotinamide (0.20 g) and 4-(ethoxymethylene)-2-methyl-1,3-oxazol-5(4H)-one (0.12 g) were dissolved in ethanol (30 mL), and the solution was stirred at room temperature for 1.5 hours. The solvent was distilled off under reduced pressure, and diisopropyl ether was added to the residue. The deposited solid was collected by filtration and washed with diisopropyl ether. The solid was dried under reduced pressure to obtain the title compound (0.015 g) as a white solid (yield: 5.5%).

MS m/z: 420 (M+H)$^+$ $^1$H-NMR (500 MHz, DMSO-$d_6$) δ: 10.44 (1H, s), 9.63 (1H, s), 9.01 (1H, s), 8.49 (1H, brs), 8.06 (1H, brs), 7.68 (2H, d, J=8 Hz), 7.22 (2H, d, J=8 Hz), 2.50-2.39 (1H, m), 2.03 (3H, s), 1.83-1.75 (4H, m), 1.74-1.67 (1H, m), 1.43-1.32 (4H, m), 1.29-1.19 (1H, m).

Example 2

6-(4-Acetamido-5-oxo-2,5-dihydro-1H-pyrazol-1-yl)-N-(4-tert-butylphenyl)nicotinamide

[Formula 12]

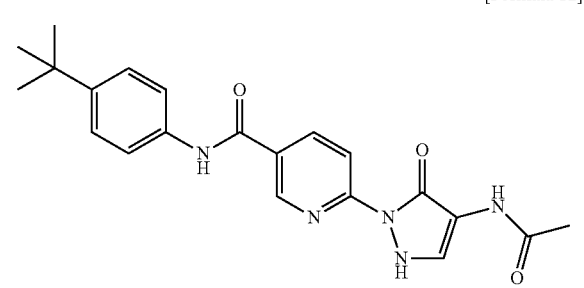

(1) 6-(4-Acetamido-5-oxo-2,5-dihydro-1H-pyrazol-1-yl)-N-(4-tert-butylphenyl)nicotinamide

[Formula 13]

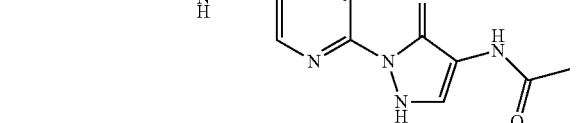

In accordance with Examples 1-(1), 1-(2), and 1-(3), but using 4-tert-butylaniline instead of 4-cyclohexylaniline, the title compound (0.073 g) was obtained as a white solid (yield: 15%).

MS m/z: 394 (M+H)$^+$ $^1$H-NMR (500 MHz, DMSO-d$_6$) δ: 10.38 (1H, brs), 9.63 (1H, brs), 9.00 (1H, s), 8.63-8.44 (2H, m), 8.13 (1H, brs), 7.68 (2H, d, J=9 Hz), 7.39 (2H, d, J=9 Hz), 2.03 (3H, s), 1.29 (9H, s).

Example 3

6-(4-Acetamido-5-oxo-2,5-dihydro-1H-pyrazol-1-yl)-N-(3-tert-butylphenyl)nicotinamide

[Formula 14]

(1) 6-(4-Acetamido-5-oxo-2,5-dihydro-1H-pyrazol-1-yl)-N-(3-tert-butylphenyl)nicotinamide

[Formula 15]

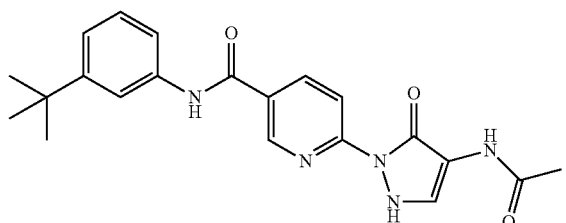

In accordance with Examples 1-(1), 1-(2), and 1-(3), but using 3-tert-butylaniline instead of 4-cyclohexylaniline, the title compound (0.048 g) was obtained (yield: 6.6%).

MS m/z: 394 (M+H)$^+$ $^1$H-NMR (500 MHz, DMSO-d$_6$) δ: 11.75 (1H, brs), 10.36 (1H, s), 9.61 (1H, s), 9.01 (1H, d, J=2 Hz), 8.59 (1H, d, J=8 Hz), 8.48 (1H, d, J=8 Hz), 8.12 (1H, s), 7.77 (1H, t, J=2 Hz), 7.66 (1H, d, J=7 Hz), 7.30 (1H, t, J=8 Hz), 7.17 (1H, d, J=8 Hz), 2.03 (3H, s), 1.30 (9H, s).

Example 4

6-(4-Acetamido-5-oxo-2,5-dihydro-1H-pyrazol-1-yl)-N-[4-(trifluoromethyl)phenyl]nicotinamide

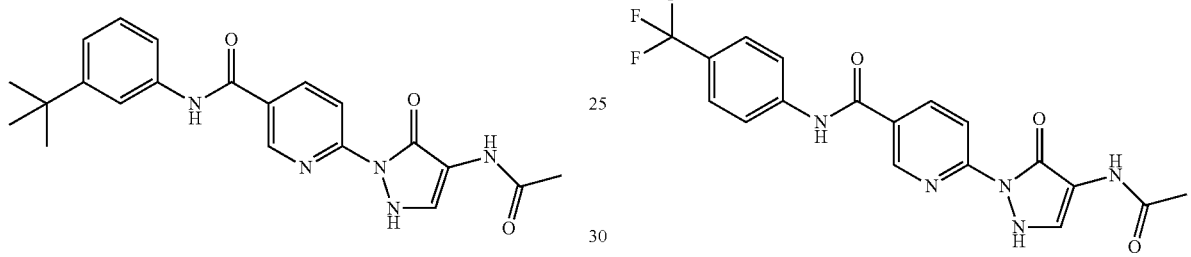

[Formula 16]

(1) 6-(4-Acetamido-5-oxo-2,5-dihydro-1H-pyrazol-1-yl)-N-[4-(trifluoromethyl)phenyl]nicotinamide

[Formula 17]

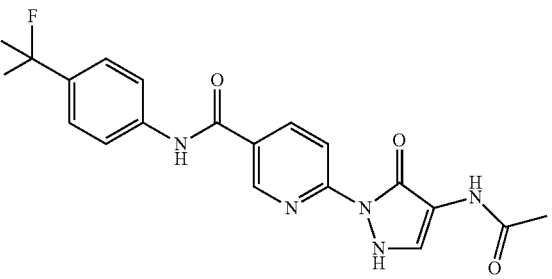

In accordance with Examples 1-(1), 1-(2), and 1-(3), but using 4-(trifluoromethyl)aniline instead of 4-cyclohexylaniline, the title compound (0.096 g) was obtained (yield: 4.3%).

MS m/z: 406 (M+H)$^+$ $^1$H-NMR (400 MHz, DMSO-d$_6$) δ: 11.75 (1H, brs), 10.76 (1H, s), 9.61 (1H, s), 9.03-9.02 (1H, m), 8.59 (1H, brs), 8.50

(1H, dd, J=9 Hz, 2 Hz), 8.11 (1H, brs), 8.02 (2H, d, J=9 Hz), 7.76 (2H, d, J=9 Hz), 2.03 (3H, s).

Example 5

6-(4-Acetamido-5-oxo-2,5-dihydro-1H-pyrazol-1-yl)-N-(4-chlorophenyl)nicotinamide

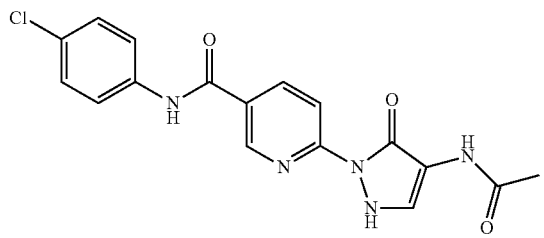

[Formula 18]

(1) 6-(4-Acetamido-5-oxo-2,5-dihydro-1H-pyrazol-1-yl)-N-(4-chlorophenyl)nicotinamide

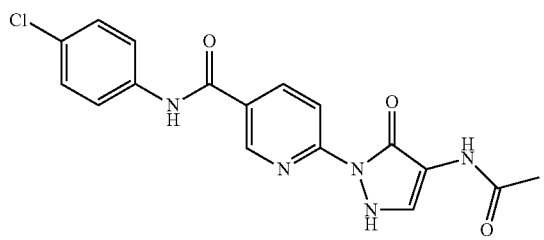

[Formula 19]

In accordance with Examples 1-(1), 1-(2), and 1-(3), but using 4-chloroaniline instead of 4-cyclohexylaniline, the title compound (0.047 g) was obtained as a yellow solid (yield: 8.2%).

MS m/z: 372 (M+H)+

$^1$H-NMR (400 MHz, DMSO-d$_6$) δ: 11.75 (2H, brs), 10.55 (1H, s), 9.52 (1H, s), 9.00 (1H, d, J=2 Hz), 8.59 (1H, d, J=9 Hz), 8.47 (1H, d, J=9 Hz), 8.13 (1H, s), 7.81 (2H, d, J=9 Hz), 7.45 (2H, d, J=9 Hz), 2.03 (3H, s).

Example 6

N-[2-(6-Morpholin-4-ylpyrimidin-4-yl)-3-oxo-2,3-dihydro-1H-pyrazol-4-yl]acetamide formate

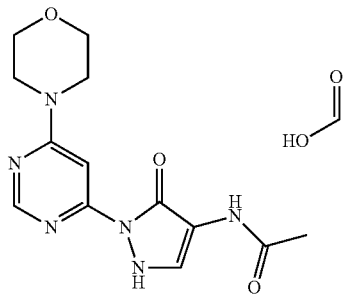

[Formula 20]

(1) N-[2-(6-Morpholin-4-ylpyrimidin-4-yl)-3-oxo-2,3-dihydro-1H-pyrazol-4-yl]acetamide formate

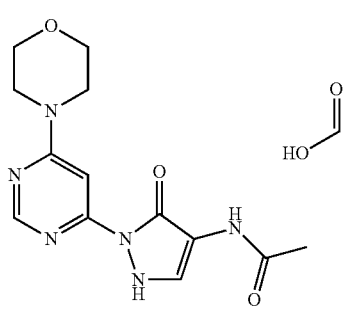

[Formula 21]

In accordance with Example 1-(3), but using 4-(6-hydrazinopyrimidin-4-yl)morpholine instead of N-(4-cyclohexylphenyl)-6-hydrazinonicotinamide, the title compound (0.11 g) was obtained as a brown solid (yield: 35%).

MS m/z: 305 (M+H)+

¹H-NMR (500 MHz, DMSO-d₆) δ: 11.61 (1H, br), 9.48 (1H, s), 8.47 (1H, s), 8.05 (1H, br), 7.74 (1H, br), 3.80-3.44 (8H, m), 2.01 (3H, s).

Example 7

N-[3-Oxo-2-(6-piperidin-1-ylpyrimidin-4-yl)-2,3-dihydro-1H-pyrazol-4-yl]acetamide formate

[Formula 22]

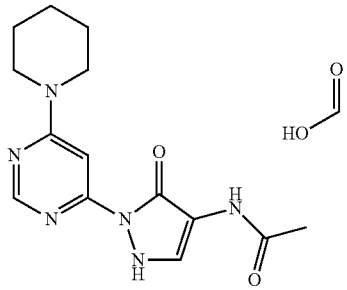

(1) N-[3-Oxo-2-(6-piperidin-1-ylpyrimidin-4-yl)-2,3-dihydro-1H-pyrazol-4-yl]acetamide formate

[Formula 23]

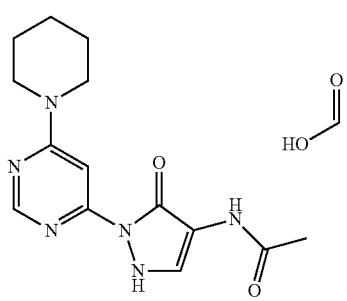

In accordance with Example 1-(3), but using 4-hydrazino-6-piperidin-1-ylpyrimidine instead of N-(4-cyclohexylphenyl)-6-hydrazinonicotinamide, the title compound (0.085 g) was obtained as a brown solid (yield: 24%).

MS m/z: 303 (M+H)⁺

¹H-NMR (400 MHz, DMSO-d₆) δ: 11.61 (1H, br), 9.44 (1H, s), 8.41 (1H, s), 8.03 (1H, br), 7.75 (1H, br), 3.64 (4H, br), 2.00 (3H, s), 1.75-1.45 (6H, m).

Example 8

N-(2-{5-[(Benzyloxy)methyl]pyridin-2-yl}-3-oxo-2,3-dihydro-1H-pyrazol-4-yl)acetamide

[Formula 24]

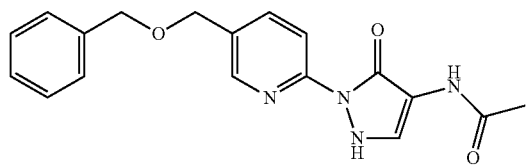

(1) N-(2-{5-[(Benzyloxy)methyl]pyridin-2-yl}-3-oxo-2,3-dihydro-1H-pyrazol-4-yl)acetamide

[Formula 25]

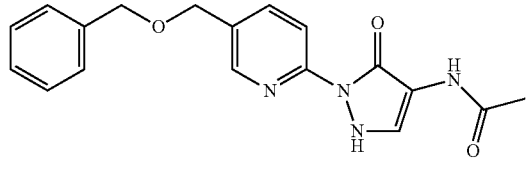

In accordance with Example 1-(3), but using 5-[(benzyloxy)methyl]-2-hydrazinopyridine instead of N-(4-cyclohexylphenyl)-6-hydrazinonicotinamide, the title compound (0.12 g) was obtained as a white solid (yield: 36%).

MS m/z: 339 (M+H)⁺

¹H-NMR (400 MHz, DMSO-d₆) δ: 11.77 (1H, br), 9.57-9.46 (1H, m), 8.43 (1H, s), 8.33 (1H, br), 7.95 (2H, br), 7.41-7.27 (5H, m), 4.57 (2H, s), 4.56 (2H, s), 2.00 (3H, s).

Example 9

N-(3-Oxo-2-{6-[(2-phenylethyl)amino]pyrimidin-4-yl}-2,3-dihydro-1H-pyrazol-4-yl)acetamide

[Formula 26]

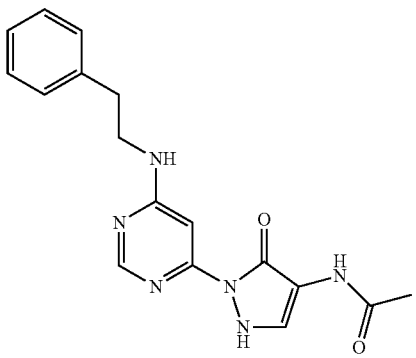

(1)
6-Hydrazino-N-(2-phenylethyl)pyrimidin-4-amine

[Formula 27]

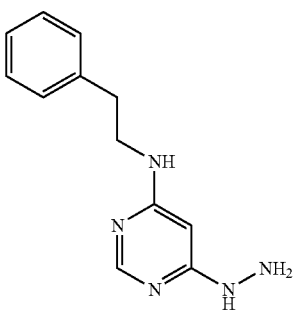

In accordance with Example 1-(2), but using 6-chloro-N-(2-phenylethyl)pyrimidin-4-amine (1.0 g) instead of 6-chloro-N-(4-cyclohexylphenyl)nicotinamide, the title compound (0.40 g) was obtained as a pale yellowish white solid (yield: 41%).

¹H-NMR (500 MHz, CDCl₃) δ: 8.08 (1H, s), 7.36-7.29 (2H, m), 7.28-7.20 (3H, m), 6.07 (1H, brs), 5.69 (1H, s), 4.88 (1H, brs), 3.52 (2H, q, J=7 Hz), 2.93 (2H, t, J=7 Hz).

(2) N-(3-Oxo-2-{6-[(2-phenylethyl)amino]pyrimidin-4-yl}-2,3-dihydro-1H-pyrazol-4-yl)acetamide

[Formula 28]

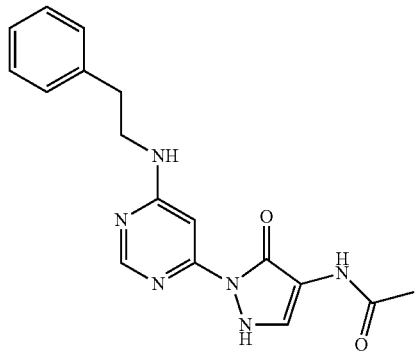

In accordance with Example 1-(3), but using 6-hydrazino-N-(2-phenylethyl)pyrimidin-4-amine (0.18 g) instead of N-(4-cyclohexylphenyl)-6-hydrazinonicotinamide, the title compound (0.12 g) was obtained as a white solid (yield: 39%).

MS m/z: 339 (M+H)⁺

¹H-NMR (500 MHz, DMSO-d₆) δ: 11.54 (1H, brs), 9.53 (1H, brs), 8.13-7.78 (2H, m), 7.51 (1H, brs), 7.36-7.11 (5H, m), 3.66-3.48 (2H, m), 2.92-2.78 (2H, m), 2.00 (3H, s).

Example 10

N-(2-{4-[(Benzyloxy)methyl]pyridin-2-yl}-3-oxo-2,3-dihydro-1H-pyrazol-4-yl)acetamide

[Formula 29]

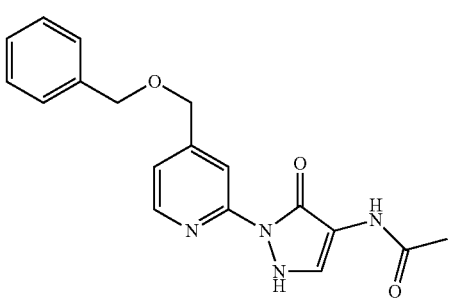

(1) N-(2-{4-[(Benzyloxy)methyl]pyridin-2-yl}-3-oxo-2,3-dihydro-1H-pyrazol-4-yl)acetamide

[Formula 30]

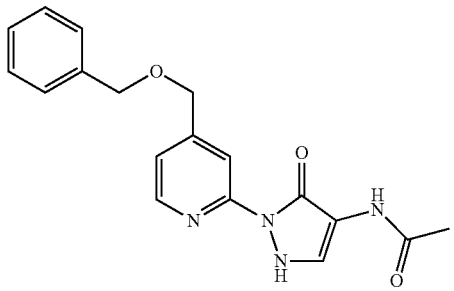

In accordance with Example 1-(3), but using 4-[(benzyloxy)methyl]-2-hydrazinopyridine instead of N-(4-cyclohexylphenyl)-6-hydrazinonicotinamide, the title compound (0.093 g) was obtained as a white solid (yield: 28%).

MS m/z: 339 (M+H)$^+$ $^1$H-NMR (400 MHz, DMSO-d$_6$) δ: 11.59 (1H, br), 9.61-9.52 (1H, m), 8.53 (1H, s), 8.41 (2H, d, J=6 Hz), 8.05 (1H, br), 7.45-7.22 (5H, m), 4.68 (2H, s), 4.61 (2H, s), 2.02 (3H, s).

Example 11

6-(4-Acetamido-5-oxo-2,5-dihydro-1H-pyrazol-1-yl)-N-(biphenyl-3-ylmethyl)nicotinamide

[Formula 31]

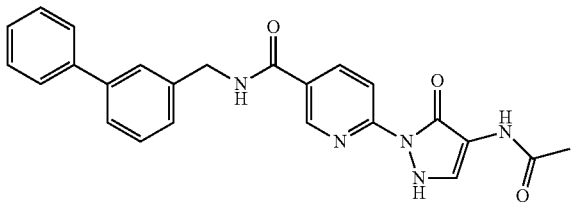

(1) N-(Biphenyl-3-ylmethyl)-6-chloronicotinamide

[Formula 32]

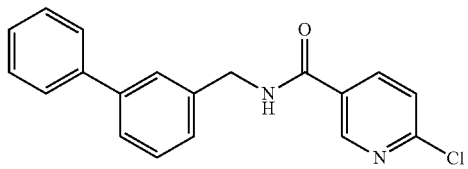

6-Chloronicotinic acid (0.29 g) and 1,1'-carbonylbis(1H-imidazole) (0.34 g) were dissolved in N,N-dimethylformamide (5 mL), and the solution was heated with stirring at 100° C. for 45 minutes. The reaction solution was brought back to room temperature. 1-Biphenyl-3-ylmethanamine (0.37 g) and triethylamine (0.51 mL) were added thereto, and the mixture was stirred at 70° C. for 2 hours. Ethyl acetate was added thereto, and the organic layer was washed with water and dried over sodium sulfate. After concentration under reduced pressure, the obtained residue was purified by silica gel column chromatography (Moritex Corporation, elution solvent: hexane/ethyl acetate) to obtain the title compound (0.48 g) as a white solid (yield: 81%).

MS m/z: 323 (M+H)$^+$ $^1$H-NMR (400 MHz, CDCl$_3$) δ: 8.77 (1H, d, J=2 Hz), 8.11 (1H, dd, J=8 Hz, 2 Hz), 7.60-7.54 (4H, m), 7.49-7.40 (4H, m), 7.39-7.33 (2H, m), 6.42 (1H, t, J=5 Hz), 4.72 (2H, d, J=5 Hz).

(2) 6-(4-Acetamido-5-oxo-2,5-dihydro-1H-pyrazol-1-yl)-N-(biphenyl-3-ylmethyl)nicotinamide

[Formula 33]

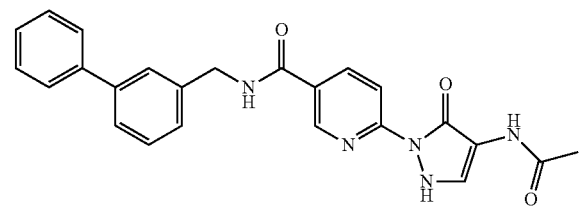

In accordance with Examples 1-(2) and 1-(3), but using N-(biphenyl-3-ylmethyl)-6-chloronicotinamide instead of 6-chloro-N-(4-cyclohexylphenyl)nicotinamide, the title compound (0.11 g) was obtained as a pale yellow solid (yield: 18%).

MS m/z: 428 (M+H)$^+$ $^1$H-NMR (400 MHz, DMSO-d$_6$) δ: 11.72 (1H, brs), 9.60 (1H, s), 9.28 (1H, t, J=5 Hz), 8.96 (1H, d, J=2 Hz), 8.54 (1H, d, J=9 Hz), 8.44 (1H, d, J=9 Hz), 8.10 (1H, s), 7.68-7.60 (3H, m), 7.56 (1H, dd, J=8 Hz, 2 Hz), 7.51-7.41 (3H, m), 7.40-7.33 (2H, m), 4.60 (2H, d, J=5 Hz), 2.02 (3H, s).

Example 12

6-(4-Acetamido-5-oxo-2,5-dihydro-1H-pyrazol-1-yl)-N-[(2'-cyanobiphenyl-4-ylmethyl)]nicotinamide

[Formula 34]

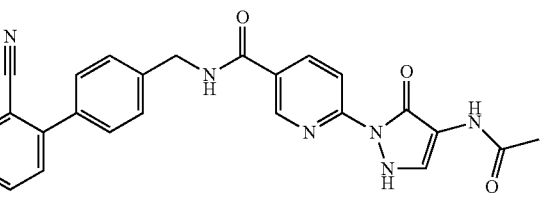

(1) 6-(4-Acetamido-5-oxo-2,5-dihydro-1H-pyrazol-1-yl)-N-[(2'-cyanobiphenyl-4-ylmethyl)]nicotinamide

[Formula 35]

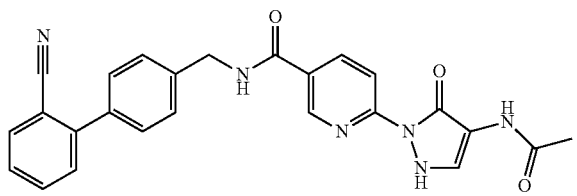

In accordance with Examples 11-(1) and 11-(2), but using 4'-(aminomethyl)biphenyl-2-carbonitrile instead of 1-biphenyl-3-ylmethanamine, the title compound (0.17 g) was obtained as a pale yellow solid (yield: 34%).

MS m/z: 453 (M+H)$^+$ $^1$H-NMR (400 MHz, DMSO-d$_6$) δ: 11.75 (1H, brs), 9.62 (1H, s), 9.34 (1H, t, J=5 Hz), 8.98 (1H, d, J=2 Hz), 8.58-8.52 (1H, m), 8.47-8.42 (1H, m), 8.11 (1H, brs), 7.96 (1H, dd, J=8 Hz, 1 Hz), 7.80 (1H, dt, J=8 Hz, 1 Hz), 7.65-7.49 (6H, m), 4.61 (2H, d, J=5 Hz), 2.02 (3H, s).

Example 13

N-[2-(5-{[(2'-Cyanobiphenyl-4-yl)methoxy]methyl}pyridin-2-yl)-3-oxo-2,3-dihydro-1H-pyrazol-4-yl]acetamide

[Formula 36]

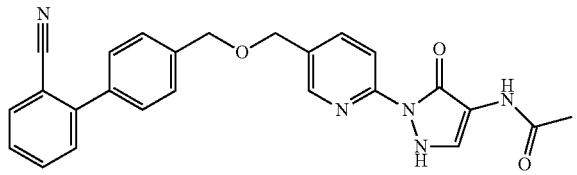

(1) 4'-{[(6-Chloropyridin-3-yl)methoxy]methyl}biphenyl-2-carbonitrile

[Formula 37]

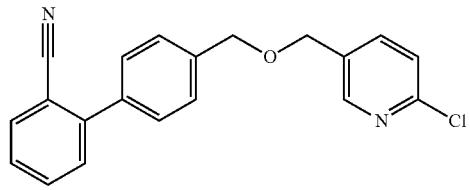

(6-Chloropyridin-3-yl)methanol (4.3 g) was dissolved in tetrahydrofuran (150 mL), and the solution was cooled to 0° C. Sodium hydride (63%, 1.4 g) was added thereto, and the mixture was stirred at 0° C. for 1 hour. Subsequently, 4'-(bromomethyl)biphenyl-2-carbonitrile (9.0 g) was added thereto at 0° C., and the mixture was stirred at 50° C. for 19 hours. The reaction solution was brought back to room temperature, and a saturated aqueous ammonium chloride solution was added thereto. After extraction with ethyl acetate, the organic layer was dried over sodium sulfate. The solvent was distilled off under reduced pressure, and the obtained residue was purified by silica gel column chromatography (Moritex Corporation, elution solvent: hexane/ethyl acetate) to obtain the title compound (6.2 g) as a white solid (yield: 62%).

$^1$H-NMR (400 MHz, CDCl$_3$) δ: 8.39 (1H, d, J=2 Hz), 7.78 (1H, d, J=8 Hz), 7.72 (1H, dd, J=8 Hz, 2 Hz), 7.66 (1H, dt, J=8 Hz, 2 Hz), 7.57 (2H, d, J=8 Hz), 7.52 (1H, d, J=8 Hz), 7.48 (2H, d, J=8 Hz), 7.45 (1H, dt, J=8 Hz, 2 Hz), 7.35 (1H, d, J=8 Hz), 4.66 (2H, s), 4.60 (2H, s).

(2) 4'-{[(6-Hydrazinopyridin-3-yl)methoxy]methyl}biphenyl-2-carbonitrile

[Formula 38]

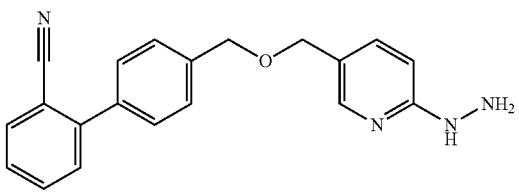

4'-{[(6-Chloropyridin-3-yl)methoxy]methyl}biphenyl-2-carbonitrile (1.7 g) and hydrazine monohydrate (3 mL) were suspended in ethanol (8 mL), and the suspension was reacted at 150° C. for 2 hours using a microwave reaction apparatus (Biotage Ltd.). The reaction solution was concentrated under reduced pressure, and the obtained residue was then purified by NH-silica gel column chromatography (Moritex Corporation, elution solvent: ethyl acetate) to obtain the title compound (0.90 g) as a yellow oil (yield: 56%).

$^1$H-NMR (400 MHz, CDCl$_3$) δ: 8.13 (1H, d, J=2 Hz), 7.77 (1H, d, J=8 Hz), 7.65 (1H, t, J=9 Hz), 7.58-7.41 (7H, m), 6.73 (1H, d, J=9 Hz), 4.60 (2H, s), 4.49 (2H, s).

(3) N-[2-(5-{[(2'-Cyanobiphenyl-4-yl)methoxy]methyl}pyridin-2-yl)-3-oxo-2,3-dihydro-1H-pyrazol-4-yl]acetamide

[Formula 39]

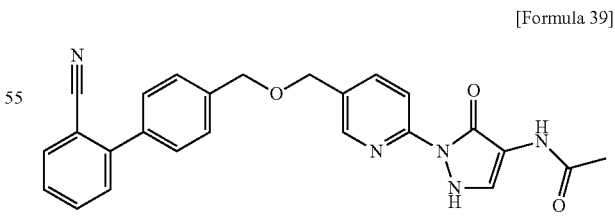

In accordance with Example 1-(3), but using 4'-{[(6-hydrazinopyridin-3-yl)methoxy]methyl}biphenyl-2-carbonitrile instead of N-(4-cyclohexylphenyl)-6-hydrazinonicotinamide, the title compound (0.11 g) was obtained as a white solid (yield: 5.5%).

MS m/z: 440 (M+H)$^+$

¹H-NMR (500 MHz, DMSO-d₆) δ: 11.63 (1H, s), 9.59 (1H, s), 8.48 (1H, brs), 8.10-7.93 (2H, m), 7.80 (1H, t, J=8 Hz), 7.66-7.50 (8H, m), 4.67 (2H, s), 4.65 (2H, s), 2.02 (3H, s).

Example 14

N-(2-{5-[(Biphenyl-4-ylmethoxy)methyl]pyridin-2-yl}-3-oxo-2,3-dihydro-1H-pyrazol-4-yl)acetamide

[Formula 40]

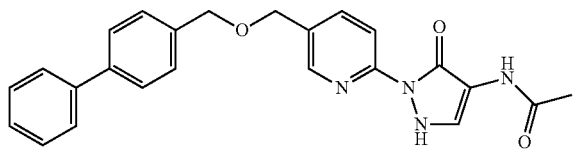

(1) N-(2-{5-[(Biphenyl-4-ylmethoxy)methyl]pyridin-2-yl}-3-oxo-2,3-dihydro-1H-pyrazol-4-yl)acetamide

[Formula 41]

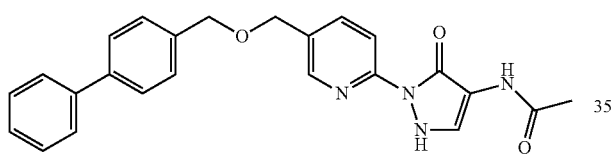

In accordance with Examples 13-(1), 13-(2), and 13-(3), but using 4-(bromomethyl)biphenyl instead of 4'-(bromomethyl)biphenyl-2-carbonitrile, the title compound (0.053 g) was obtained as a pale yellow solid (yield: 37%).

MS m/z: 415 (M+H)⁺

¹H-NMR (400 MHz, DMSO-d₆) δ: 11.62 (1H, s), 8.52-8.45 (2H, m), 8.10-7.96 (2H, m), 7.74-7.66 (4H, m), 7.53-7.45 (4H, m), 7.36 (1H, t, J=8 Hz), 4.61 (4H, s), 2.01 (3H, s).

Example 15

N-(2-{5-[(Biphenyl-3-ylmethoxy)methyl]pyridin-2-yl}-3-oxo-2,3-dihydro-1H-pyrazol-4-yl)acetamide

[Formula 42]

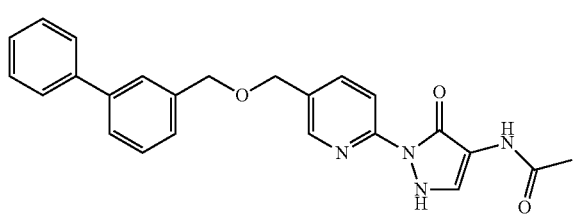

(1) N-(2-{5-[(Biphenyl-3-ylmethoxy)methyl]pyridin-2-yl}-3-oxo-2,3-dihydro-1H-pyrazol-4-yl)acetamide

[Formula 43]

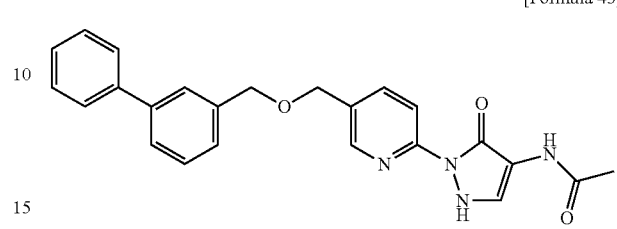

In accordance with Examples 13-(1), 13-(2), and 13-(3), but using 3-(bromomethyl)biphenyl instead of 4'-(bromomethyl)biphenyl-2-carbonitrile, the title compound (0.14 g) was obtained as a pale yellow solid (yield: 19%).

MS m/z: 415 (M+H)⁺

¹H-NMR (400 MHz, DMSO-d₆) δ: 9.58 (1H, s), 8.47-8.45 (2H, m), 8.09-7.95 (2H, m), 7.69-7.58 (5H, m), 7.50-7.45 (3H, m), 7.40-7.35 (2H, m), 4.65 (2H, s), 4.63 (2H, s), 2.01 (3H, s).

Example 16

6-(4-Acetamido-3-methyl-5-oxo-2,5-dihydro-1H-pyrazol-1-yl)-N-[4-(trifluoromethyl)phenyl]nicotinamide

[Formula 44]

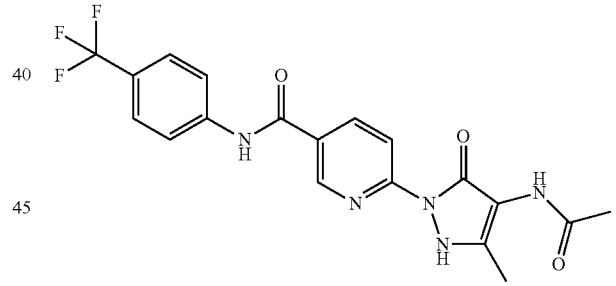

(1) 6-Chloro-N-[4-(trifluoromethyl)phenyl]nicotinamide

[Formula 45]

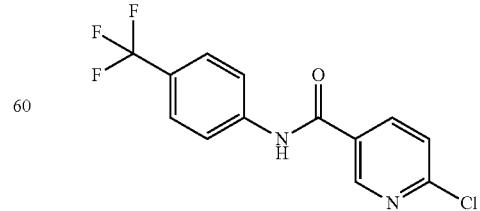

6-Chloronicotinoyl chloride (0.83 g) was dissolved in toluene (15 mL), and the solution was cooled to 0° C. 4-(Trifluoromethyl)aniline (1.6 g) was added thereto at 0° C., and the mixture was stirred at room temperature for 10 hours. Ethyl acetate was added thereto, and the organic layer was washed with a 1 N aqueous sodium hydroxide solution and water and dried over sodium sulfate. After concentration under reduced pressure, the obtained solid was collected by filtration and washed with diethyl ether. The solid was dried under reduced pressure to obtain the title compound (0.88 g) as a white solid (yield: 29%).

MS m/z: 301 (M+H)$^+$ $^1$H-NMR (400 MHz, CDCl$_3$) δ: 8.88 (1H, d, J=2 Hz), 8.20 (1H, dd, J=8 Hz, 2 Hz), 7.86 (1H, brs), 7.78 (2H, d, J=9 Hz), 7.67 (1H, d, J=8 Hz), 7.51 (2H, d, J=9 Hz).

(2) 6-Hydrazino-N-[4-(trifluoromethyl)phenyl]nicotinamide

[Formula 46]

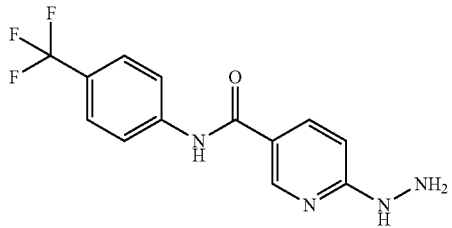

6-Chloro-N-[4-(trifluoromethyl)phenyl]nicotinamide (0.49 g) and hydrazine monohydrate (4 mL) were suspended in ethanol (8 mL), and the suspension was heated to reflux for 15 hours. The reaction solution was concentrated under reduced pressure, and the obtained solid was then collected by filtration and washed with ethyl acetate. The solid was dried under reduced pressure to obtain the title compound (0.31 g) as a white solid (yield: 64%).

MS m/z: 297 (M+H)$^+$ $^1$H-NMR (400 MHz, DMSO-d$_6$) δ: 10.26 (1H, s), 8.66 (1H, d, J=2 Hz), 8.26 (1H, brs), 8.02 (1H, dd, J=9 Hz, 2 Hz), 7.98 (2H, d, J=8 Hz), 7.70 (2H, d, J=8 Hz), 6.76 (1H, d, J=9 Hz), 4.38 (2H, brs).

(3) 6-(4-Acetamido-3-methyl-5-oxo-2,5-dihydro-1H-pyrazol-1-yl)-N-[4-(trifluoromethyl)phenyl]nicotinamide

[Formula 47]

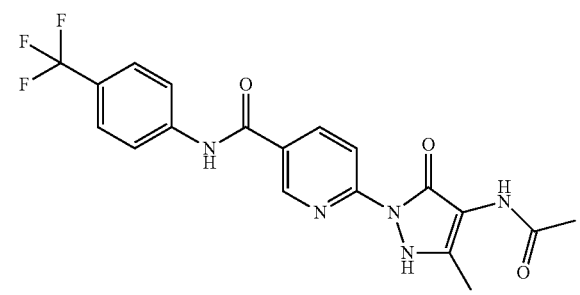

6-Hydrazino-N-[4-(trifluoromethyl)phenyl]nicotinamide (0.31 g) and ethyl 2-acetamido-3-oxobutanoate (0.24 g) were suspended in ethanol (25 mL), and the suspension was heated to reflux for 23 hours. The reaction solution was cooled to room temperature, and the obtained solid was collected by filtration and washed with ethanol. The solid was dried under reduced pressure to obtain the title compound (0.20 g) as a white solid (yield: 46%).

MS m/z: 420 (M+H)$^+$ $^1$H-NMR (400 MHz, DMSO-d$_6$) δ: 12.13 (1H, brs), 10.74 (1H, s), 8.99 (2H, m), 8.59-8.42 (2H, m), 8.00 (2H, d, J=8 Hz), 7.76 (2H, d, J=8 Hz), 2.09 (3H, s), 1.90 (3H, s).

Example 17

6-(4-Acetamido-3-methyl-5-oxo-2,5-dihydro-1H-pyrazol-1-yl)-N-(4-chlorophenyl)nicotinamide

[Formula 48]

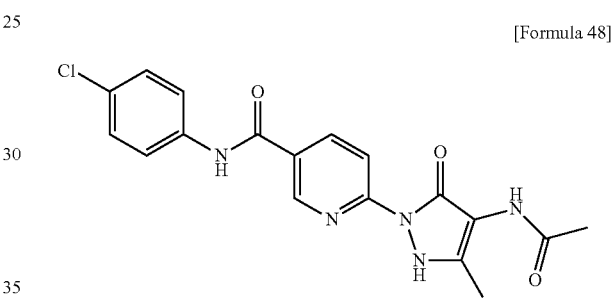

(1) 6-(4-Acetamido-3-methyl-5-oxo-2,5-dihydro-1H-pyrazol-1-yl)-N-(4-chlorophenyl)nicotinamide

[Formula 49]

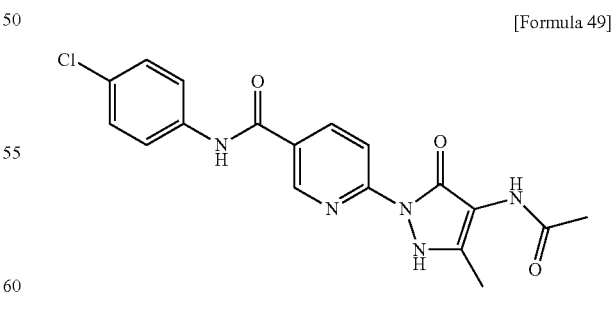

In accordance with Examples 16-(1), 16-(2), and 16-(3), but using 4-chloroaniline instead of 4-(trifluoromethyl)aniline, the title compound (0.21 g) was obtained as a white solid (yield: 17%).

MS m/z: 386 (M+H)$^+$

¹H-NMR (400 MHz, DMSO-d₆) δ: 12.12 (1H, brs), 10.53 (1H, s), 8.95 (2H, m), 8.54 (1H, d, J=9 Hz), 8.43 (1H, d, J=8 Hz), 7.80 (2H, d, J=8 Hz), 7.44 (2H, d, J=8 Hz), 2.09 (3H, s), 1.98 (3H, s).

Example 18

6-(4-Acetamido-3-methyl-5-oxo-2,5-dihydro-1H-pyrazol-1-yl)-N-(4-bromophenyl)nicotinamide

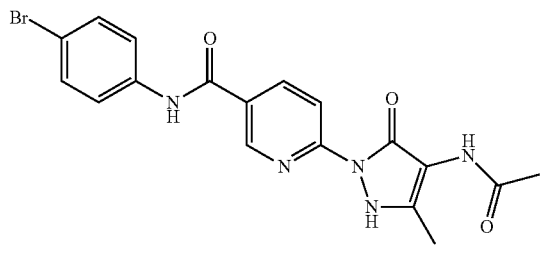

[Formula 50]

(1) 6-(4-Acetamido-3-methyl-5-oxo-2,5-dihydro-1H-pyrazol-1-yl)-N-(4-bromophenyl)nicotinamide

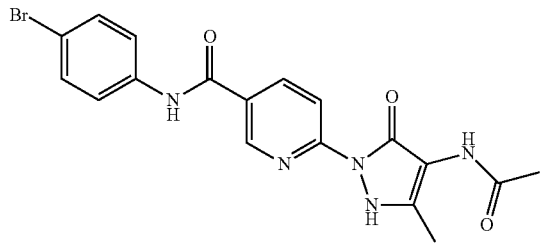

[Formula 51]

In accordance with Examples 16-(1), 16-(2), and 16-(3), but using 4-bromoaniline instead of 4-(trifluoromethyl)aniline, the title compound (0.24 g) was obtained as a pale red solid (yield: 31%).

MS m/z: 430 (M+H)⁺

¹H-NMR (400 MHz, DMSO-d₆) δ: 12.12 (1H, brs), 10.53 (1H, s), 8.97 (2H, m), 8.54 (1H, d, J=9 Hz), 8.43 (1H, d, J=8 Hz), 7.75 (2H, d, J=8 Hz), 7.57 (2H, d, J=8 Hz), 2.09 (3H, s), 1.98 (3H, s).

Example 19

6-(4-Acetamido-3-methyl-5-oxo-2,5-dihydro-1H-pyrazol-1-yl)-N-(4-tert-butylphenyl)nicotinamide

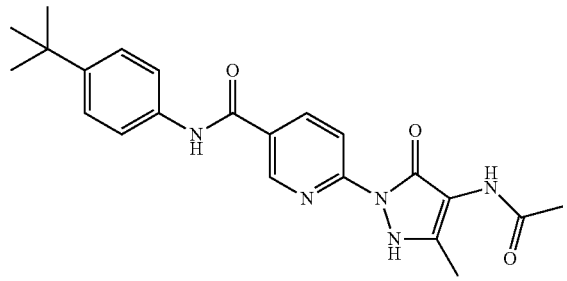

[Formula 52]

(1) 6-(4-Acetamido-3-methyl-5-oxo-2,5-dihydro-1H-pyrazol-1-yl)-N-(4-tert-butylphenyl)nicotinamide

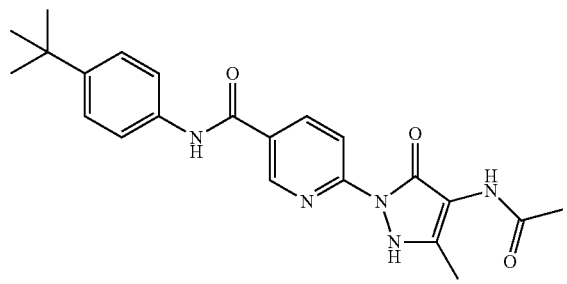

[Formula 53]

In accordance with Examples 16-(1), 16-(2), and 16-(3), but using 4-tert-butylaniline instead of 4-(trifluoromethyl)aniline, the title compound (0.57 g) was obtained as a white solid (yield: 29%).

MS m/z: 408 (M+H)⁺

¹H-NMR (400 MHz, DMSO-d₆) δ: 12.11 (1H, brs), 10.35 (1H, s), 8.96 (2H, m), 8.53 (1H, d, J=9 Hz), 8.44 (1H, d, J=8 Hz), 7.67 (2H, d, J=8 Hz), 7.39 (2H, d, J=8 Hz), 2.09 (3H, s), 1.98 (3H, s), 1.29 (9H, s).

Example 20

6-(4-Acetamido-3-methyl-5-oxo-2,5-dihydro-1H-pyrazol-1-yl)-N-(6-phenylpyridin-3-yl)nicotinamide

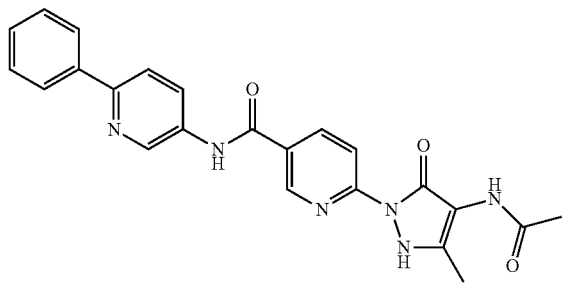

[Formula 54]

(1) 6-(4-Acetamido-3-methyl-5-oxo-2,5-dihydro-1H-pyrazol-1-yl)-N-(6-phenylpyridin-3-yl)nicotinamide

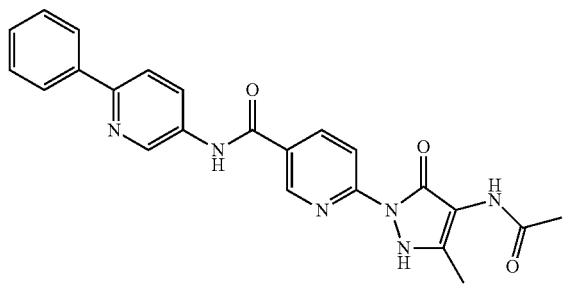

[Formula 55]

In accordance with Examples 16-(1), 16-(2), and 16-(3), but using 6-phenylpyridin-3-amine instead of 4-(trifluoromethyl)aniline, the title compound (0.24 g) was obtained as a white solid (yield: 37%).

MS m/z: 429 (M+H)⁺

¹H-NMR (400 MHz, DMSO-d₆) δ: 12.14 (1H, brs), 10.72 (1H, s), 9.05-8.96 (3H, m), 8.56 (1H, d, J=9 Hz), 8.49 (1H, d, J=8 Hz), 8.29 (1H, dd, J=8 Hz, 2 Hz), 8.09 (2H, d, J=7 Hz), 8.03 (1H, d, J=9 Hz), 7.50 (2H, t, J=7 Hz), 7.42 (1H, t, J=7 Hz), 2.10 (3H, s), 1.98 (3H, s).

Example 21

N-[2-(5-{[(2'-Cyanobiphenyl-4-yl)methoxy]methyl}pyridin-2-yl)-5-methyl-3-oxo-2,3-dihydro-1H-pyrazol-4-yl]acetamide

[Formula 56]

(1) N-[2-(5-{[(2'-Cyanobiphenyl-4-yl)methoxy]methyl}pyridin-2-yl)-5-methyl-3-oxo-2,3-dihydro-1H-pyrazol-4-yl]acetamide

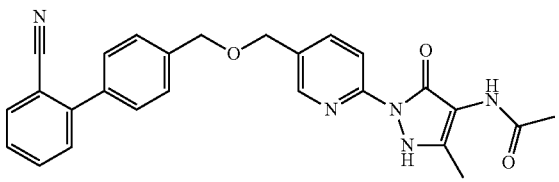

[Formula 57]

In accordance with Example 16-(3), but using 4'-{[(6-hydrazinopyridin-3-yl)methoxy]methyl}biphenyl-2-carbonitrile instead of 6-hydrazino-N-[4-(trifluoromethyl)phenyl]nicotinamide, the title compound (0.91 g) was obtained as a white solid (yield: 74%).

MS m/z: 454 (M+H)⁺

¹H-NMR (400 MHz, DMSO-d₆) δ: 11.95 (1H, s), 8.94 (1H, s), 8.45 (1H, d, J=2 Hz), 7.96 (1H, dd, J=6 Hz, 2 Hz), 7.80 (1H, dt, J=6 Hz, 2 Hz), 7.66-7.50 (8H, m), 4.67 (2H, s), 4.65 (2H, s), 2.06 (3H, s), 1.97 (3H, s).

Example 22

Tert-butyl 4-[(5-methyl-3-oxo-2-{5-[(6-phenylpyridyl-3-yl)carbamoyl]pyridin-2-yl}-2,3-dihydro-1H-pyrazol-4-yl)amino]-4-oxobutanoate

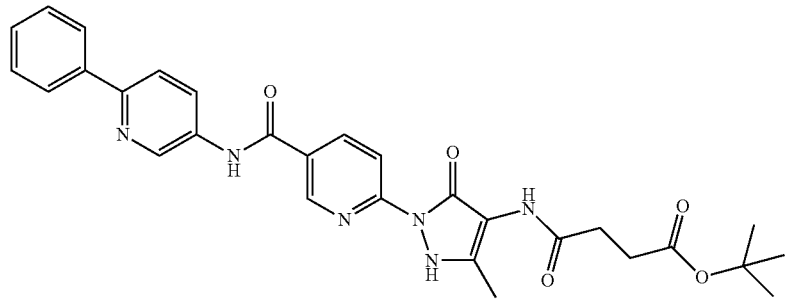

[Formula 58]

(1) Ethyl 2-[(4-tert-butoxy-4-oxobutanoyl)amino]-3-oxobutanoate

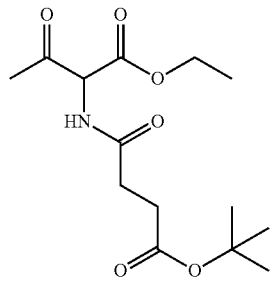

[Formula 59]

4-Tert-butoxy-4-oxobutanoic acid (1.7 g) and N-methylmorpholine (1.1 mL) were dissolved in tetrahydrofuran (60 mL), and the solution was cooled to 0° C. Isobutyl chloroformate (1.3 mL) was added thereto, and the mixture was stirred at 0° C. for 30 minutes. A solution of ethyl 2-amino-3-oxobutanoate hydrochloride (1.8 g) in N,N-dimethylformamide (30 mL) was added thereto, and the mixture was stirred at 0° C. for 5 minutes. Then, N-methylmorpholine (1.1 mL) was added thereto, and the mixture was stirred at room temperature for 20 hours. Ethyl acetate was added to the reaction solution, and the organic layer was washed with water and dried over sodium sulfate. The solvent was distilled off under reduced pressure, and the obtained residue was purified by silica gel column chromatography (Moritex Corporation, elution solvent: hexane/ethyl acetate) to obtain the title compound (2.2 g) as a yellow oil (yield: 72%).

MS m/z: 300 (M−H)$^+$ $^1$H-NMR (400 MHz, CDCl$_3$) δ: 6.79 (1H, d, J=6 Hz), 5.23 (1H, d, J=6 Hz), 4.27 (2H, q, J=7 Hz), 2.62-2.50 (4H, m), 2.38 (3H, s), 1.44 (9H, s), 1.31 (3H, t, J=7 Hz).

(2) Tert-butyl 4-[(5-methyl-3-oxo-2-{5-[(6-phenylpyridyl-3-yl)carbamoyl]pyridin-2-yl}-2,3-dihydro-1H-pyrazol-4-yl)amino]-4-oxobutanoate

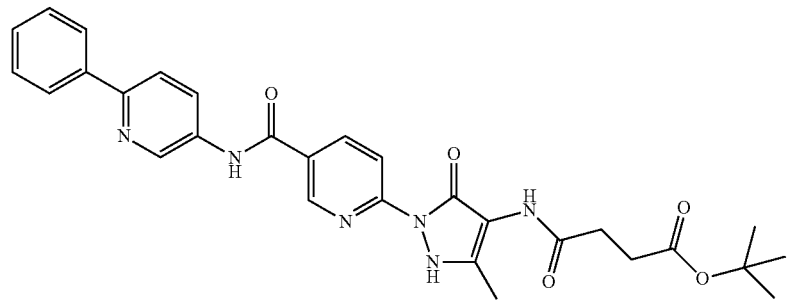

[Formula 60]

In accordance with Examples 16-(1), 16-(2), and 16-(3), but using 6-phenylpyridin-3-amine instead of 4-(trifluoromethyl)aniline and ethyl 2-[(4-tert-butoxy-4-oxobutanoyl)amino]-3-oxobutanoate instead of ethyl 2-acetamido-3-oxobutanoate, the title compound (0.24 g) was obtained as a white solid (yield: 30%).

MS m/z: 543 (M+H)$^+$ $^1$H-NMR (400 MHz, DMSO-d$_6$) δ: 12.14 (1H, brs), 10.72 (1H, s), 9.05-8.99 (3H, m), 8.57 (1H, d, J=9 Hz), 8.48 (1H, d, J=8 Hz), 8.29 (1H, dd, J=8 Hz, 2 Hz), 8.09 (2H, d, J=7 Hz), 8.02 (1H, d, J=9 Hz), 7.49 (2H, t, J=7 Hz), 7.42 (1H, t, J=7 Hz), 2.54-2.46 (4H, m), 2.08 (3H, s), 1.40 (9H, s).

Example 23

4-[(5-Methyl-3-oxo-2-{5-[(6-phenylpyridyl-3-yl)carbamoyl]pyridin-2-yl}-2,3-dihydro-1H-pyrazol-4-yl)amino]-4-oxobutanoic acid

[Formula 61]

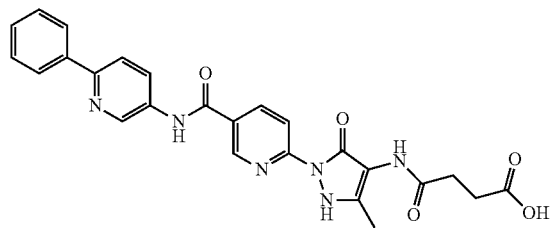

(1) 4-[(5-Methyl-3-oxo-2-{5-[(6-phenylpyridyl-3-yl)carbamoyl]pyridin-2-yl}-2,3-dihydro-1H-pyrazol-4-yl)amino]-4-oxobutanoic acid

[Formula 62]

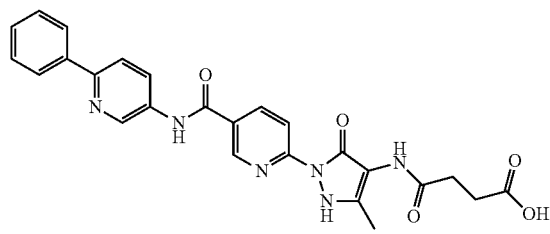

Tert-butyl 4-[(5-methyl-3-oxo-2-{5-[(6-phenylpyridyl-3-yl)carbamoyl]pyridin-2-yl}-2,3-dihydro-1H-pyrazol-4-yl)amino]-4-oxobutanoate (0.054 g) was dissolved in dichloromethane (10 mL). To the solution, trifluoroacetic acid (1.0 mL) was added at room temperature, and the mixture was stirred for 20 hours. The solvent was distilled off under reduced pressure, and the pH of the residue was adjusted to pH 6 by the addition of a saturated aqueous sodium hydrogencarbonate solution. The obtained solid was collected by filtration and washed with water. The solid was dried under reduced pressure to obtain the title compound (0.047 g) as a yellow solid (yield: 97%).

MS m/z: 487 (M+H)$^+$ $^1$H-NMR (400 MHz, DMSO-d$_6$) δ: 10.73 (1H, s), 9.05-8.99 (3H, m), 8.57-8.44 (2H, m), 8.29 (1H, dd, J=8 Hz, 2 Hz), 8.09 (2H, d, J=7 Hz), 8.02 (1H, d, J=9 Hz), 7.49 (2H, t, J=7 Hz), 7.43 (1H, t, J=7 Hz), 2.51 (4H, s), 2.07 (3H, s).

Example 24

N-{5-Methyl-3-oxo-2-[5-({[4-(trifluoromethyl)benzyl]oxy}methyl)pyridin-2-yl]-2,3-dihydro-1H-pyrazol-4-yl}acetamide

[Formula 63]

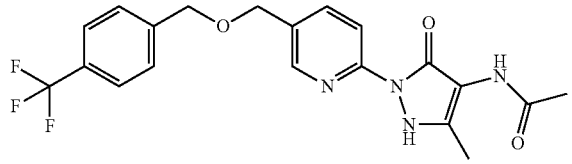

(1) N-{5-Methyl-3-oxo-2-[5-({[4-(trifluoromethyl)benzyl]oxy}methyl)pyridin-2-yl]-2,3-dihydro-1H-pyrazol-4-yl}acetamide

[Formula 64]

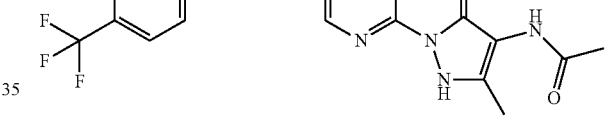

In accordance with Examples 13-(1), 13-(2), and 16-(3), but using 1-(bromomethyl)-4-(trifluoromethyl)benzene instead of 4'-(bromomethyl)biphenyl-2-carbonitrile, the title compound (0.11 g) was obtained as a white solid (yield: 19%).

MS m/z: 421 (M+H)$^+$ $^1$H-NMR (400 MHz, DMSO-d$_6$) δ: 11.97 (1H, s), 8.96 (1H, s), 8.43 (1H, s), 8.42 (1H, d, J=8 Hz), 7.95 (1H, d, J=8 Hz), 7.74 (2H, d, J=8 Hz), 7.60 (2H, d, J=8 Hz), 4.68 (2H, s), 4.61 (2H, s), 2.06 (3H, s), 1.97 (3H, s).

Example 25

N-(5-Methyl-3-oxo-2-{5-[4-(trifluoromethyl)benzyl]pyridin-2-yl}-2,3-dihydro-1H-pyrazol-4-yl)acetamide

[Formula 65]

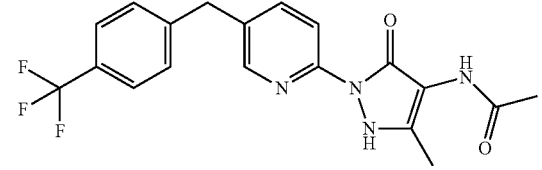

53

(1) 2-Hydrazinyl-5-[4-(trifluoromethyl)benzyl]pyridine

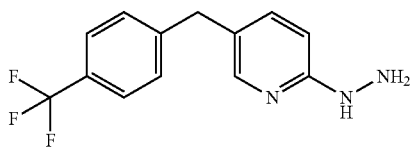

[Formula 66]

In accordance with Example 13-(2), but using 2-chloro-5-[4-(trifluoromethyl)benzyl]pyridine instead of 4'-{[(6-chloropyridin-3-yl)methoxy]methyl}biphenyl-2-carbonitrile, the title compound (0.41 g) was obtained (yield: 47%).

$^1$H-NMR (400 MHz, CDCl$_3$) δ: 8.01 (1H, s), 7.54 (1H, d, J=8 Hz), 7.31-7.24 (5H, m), 6.68 (1H, d, J=8 Hz), 5.73 (1H, brs), 3.91 (2H, s), 3.82 (2H, brs).

(2) N-(5-Methyl-3-oxo-2-{5-[4-(trifluoromethyl)benzyl]pyridin-2-yl}-2,3-dihydro-1H-pyrazol-4-yl)acetamide

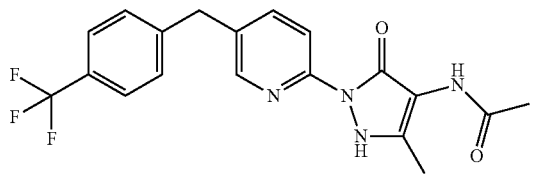

[Formula 67]

In accordance with Example 16-(3), but using 2-hydrazinyl-5-[4-(trifluoromethyl)benzyl]pyridine instead of 6-hydrazino-N-[4-(trifluoromethyl)phenyl]nicotinamide, the title compound (0.057 g) was obtained as a white solid (yield: 9.5%).

MS m/z: 391 (M+H)$^+$

54

$^1$H-NMR (400 MHz, DMSO-d$_6$) δ: 11.91 (1H, s), 8.94 (1H, s), 8.40 (1H, s), 8.34 (1H, m), 7.80 (1H, m), 7.68 (2H, d, J=8 Hz), 7.50 (2H, d, J=8 Hz), 4.10 (2H, s), 2.05 (3H, s), 1.96 (3H, s).

Example 26

N-[5-Methyl-3-oxo-2-(5-{2-[4-(trifluoromethyl)phenyl]ethyl}pyridin-2-yl)-2,3-dihydro-1H-pyrazol-4-yl]acetamide

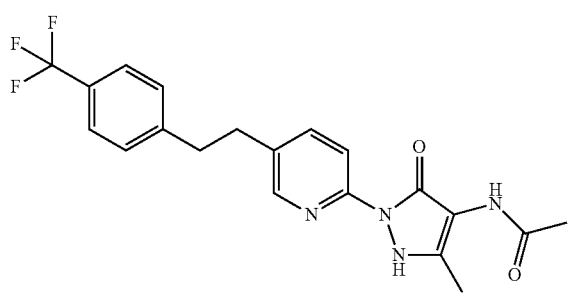

[Formula 68]

(1) 2-Chloro-5-{(E)-2-[4-(trifluoromethyl)phenyl]ethenyl}pyridine

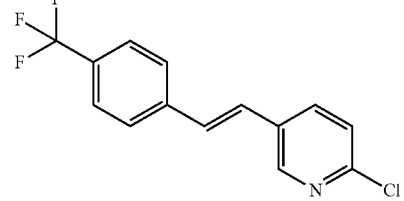

[Formula 69]

Triphenyl[4-(trifluoromethyl)benzyl]phosphonium bromide (6.4 g) and 6-chloropyridine-3-carboxaldehyde (1.8 g) were dissolved in ethanol (120 mL). To the solution, sodium tert-butoxide (1.2 g) was added at room temperature, and the mixture was stirred for 1 hour. The solvent was distilled off under reduced pressure, and ethyl acetate was added to the residue. The organic layer was washed with water and dried over sodium sulfate. The solvent was distilled off under reduced pressure, and the obtained residue was purified by silica gel column chromatography (Yamazen Corporation, elution solvent: hexane/ethyl acetate). The obtained solid was washed with hexane to obtain the title compound (0.89 g) (yield: 25%).

¹H-NMR (400 MHz, CDCl₃) δ: 8.51 (1H, d, J=2 Hz), 7.84 (1H, dd, J=8 Hz, 2 Hz), 7.67-7.59 (4H, m), 7.35 (1H, d, J=8 Hz), 7.15 (1H, s), 7.14 (1H, s).

(2) Di-tert-butyl 1-(5-{(E)-2-[4-(trifluoromethyl)phenyl]ethenyl}pyridin-2-yl)hydrazine-1,2-dicarbonate

[Formula 70]

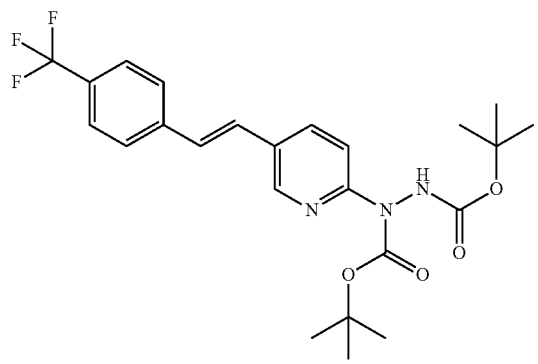

2-Chloro-5-{(E)-2-[4-(trifluoromethyl)phenyl]ethenyl}pyridine (0.77 g) was dissolved in toluene (15 mL). To the solution, di-tert-butyl hydrazine-1,2-dicarbonate (0.63 g), tris(dibenzylideneacetone)dipalladium complex (0.20 g), 1,1'-bis(diphenylphosphino)ferrocene (0.18 g), and cesium carbonate (2.7 g) were added at room temperature, and the mixture was stirred at 100° C. for 24 hours. Insoluble matter was filtered off through celite, and the filtrate was concentrated under reduced pressure. The obtained residue was purified by silica gel column chromatography (Moritex Corporation, elution solvent: hexane/ethyl acetate) to obtain the title compound (0.72 g) (yield: 55%).

MS m/z: 480 (M+H)⁺

¹H-NMR (400 MHz, CDCl₃) δ: 8.48 (1H, d, J=2 Hz), 7.87 (1H, dd, J=8 Hz, 2 Hz), 7.78 (1H, d, J=8 Hz), 7.61 (4H, s), 7.12 (1H, s), 7.11 (1H, s), 7.00 (1H, brs), 1.54 (9H, s), 1.48 (9H, s).

(3) Di-tert-butyl 1-(5-{2-[4-(trifluoromethyl)phenyl]ethyl}pyridin-2-yl)hydrazine-1,2-dicarbonate

[Formula 71]

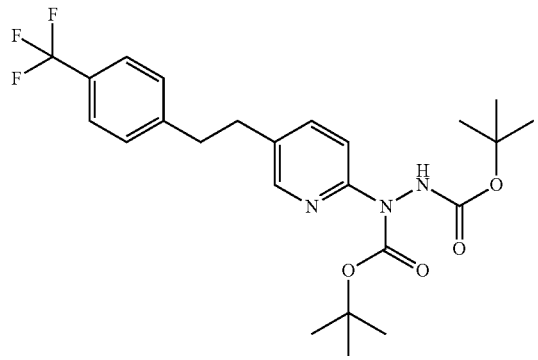

Di-tert-butyl 1-(5-{(E)-2-[4-(trifluoromethyl)phenyl]ethenyl}pyridin-2-yl)hydrazine-1,2-dicarbonate (0.40 g) was dissolved in ethyl acetate (20 mL). To the solution, palladium-carbon was added, and the mixture was stirred at room temperature for 10 hours under a hydrogen atmosphere. Insoluble matter was filtered off through celite, and the filtrate was concentrated under reduced pressure. The obtained residue was purified by silica gel column chromatography (Yamazen Corporation, elution solvent: hexane/ethyl acetate) to obtain the title compound (0.32 g) (yield: 81%).

¹H-NMR (400 MHz, CDCl₃) δ: 8.15 (1H, d, J=2 Hz), 7.62 (1H, d, J=8 Hz), 7.53 (2H, d, J=10 Hz), 7.44 (1H, dd, J=8 Hz, 2 Hz), 7.25 (2H, d, J=10 Hz), 6.99 (1H, brs), 3.00-2.86 (4H, m), 1.52 (9H, s), 1.47 (9H, s).

(4) 2-Hydrazinyl-5-{2-[4-(trifluoromethyl)phenyl]ethyl}pyridine

[Formula 72]

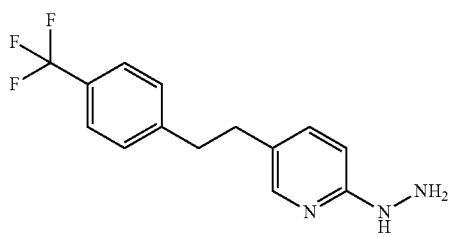

Di-tert-butyl 1-(5-{2-[4-(trifluoromethyl)phenyl]ethyl}pyridin-2-yl)hydrazine-1,2-dicarbonate (0.44 g) was dissolved in a solution of hydrogen chloride in dioxane (4 N, 10 mL), and the solution was stirred at room temperature for 12 hours. A saturated aqueous sodium hydrogencarbonate solution was added to the reaction solution, followed by extraction with dichloromethane. The organic layer was dried over sodium sulfate. The solvent was distilled off under reduced pressure, and the obtained residue was purified by NH-silica gel column chromatography (Moritex Corporation, elution solvent: hexane/ethyl acetate) to obtain the title compound (0.26 g) (yield: 74%).

MS m/z: 282 (M+H)⁺

¹H-NMR (500 MHz, CDCl₃) δ: 7.90 (1H, d, J=2 Hz), 7.52 (2H, d, J=8 Hz), 7.29-7.22 (3H, m), 6.65 (1H, d, J=9 Hz), 5.71 (1H, brs), 3.78 (2H, brs), 2.95-2.90 (2H, m), 2.85-2.80 (2H, m).

(5) N-[5-Methyl-3-oxo-2-(5-{2-[4-(trifluoromethyl)phenyl]ethyl}pyridin-2-yl)-2,3-dihydro-1H-pyrazol-4-yl]acetamide

[Formula 73]

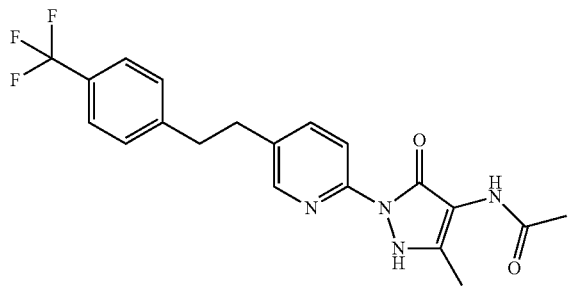

In accordance with Example 16-(3), but using 2-hydrazinyl-5-{2-[4-(trifluoromethyl)phenyl]ethyl}pyridine instead of di-tert-butyl 1-{5-[4-(trifluoromethyl)phenyl]pyridin-2-yl}hydrazine-1,2-dicarbonate, the title compound (0.15 g) was obtained as a white solid (yield: 56%).

MS m/z: 405 (M+H)⁺

¹H-NMR (400 MHz, DMSO-d₆) δ: 11.88 (1H, brs), 8.92 (1H, s), 8.32 (1H, d, J=7 Hz), 8.20 (1H, d, J=2 Hz), 7.81 (1H, dd, J=7 Hz, 2 Hz), 7.64 (2H, d, J=9 Hz), 7.44 (2H, d, J=9 Hz), 3.05-2.92 (4H, m), 2.04 (3H, s), 1.96 (3H, s).

Example 27

N-[5-Methyl-3-oxo-2-(5-{(E)-2-[4-(trifluoromethyl)phenyl]ethenyl}pyridin-2-yl)-2,3-dihydro-1H-pyrazol-4-yl]acetamide

[Formula 74]

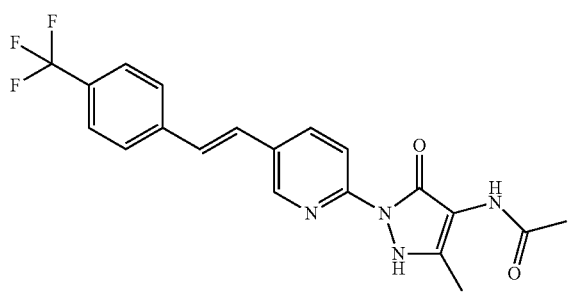

(1) 2,2,2-Trifluoro-N-(5-{(E)-2-[4-(trifluoromethyl)phenyl]ethenyl}pyridin-2-yl)acetohydrazide

[Formula 75]

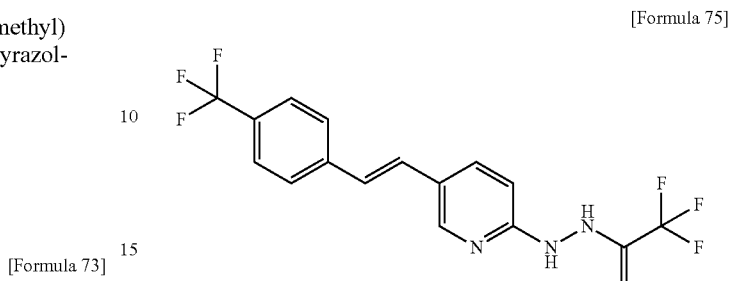

Di-tert-butyl 1-(5-{(E)-2-[4-(trifluoromethyl)phenyl]ethenyl}pyridin-2-yl)hydrazine-1,2-dicarbonate (0.32 g) was dissolved in dichloromethane (10 mL). To the solution, trifluoroacetic acid (3 mL) was added at room temperature, and the mixture was stirred for 17 hours. After concentration under reduced pressure, a saturated aqueous sodium hydrogencarbonate solution was added to the residue. The obtained solid was collected by filtration and washed with water. The solid was dried under reduced pressure to obtain the title compound (0.18 g) (yield: 71%).

MS m/z: 376 (M+H)⁺

¹H-NMR (400 MHz, DMSO-d₆) δ: 11.54 (1H, brs), 9.15 (1H, brs), 8.22 (1H, s), 7.94 (1H, d, J=9 Hz), 7.79-7.68 (4H, m), 7.34 (1H, d, J=17 Hz), 7.17 (1H, d, J=17 Hz), 6.78 (1H, d, J=9 Hz).

(2) 2-Hydrazinyl-5-{(E)-2-[4-(trifluoromethyl)phenyl]ethenyl}pyridine

[Formula 76]

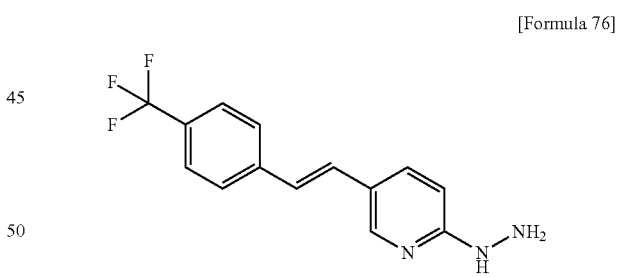

2,2,2-Trifluoro-N-(5-{(E)-2-[4-(trifluoromethyl)phenyl]ethenyl}pyridin-2-yl)acetohydrazide (0.17 g) was dissolved in ethanol (5 mL). To the solution, concentrated hydrochloric acid (1 mL) was added at room temperature, and the mixture was heated to reflux for 2 hours. A saturated aqueous sodium hydrogencarbonate solution was added to the reaction solution, followed by extraction with dichloromethane. The organic layer was dried over sodium sulfate. The solvent was distilled off under reduced pressure, and the obtained residue was purified by NH-silica gel column chromatography (Moritex Corporation, elution solvent: ethyl acetate) to obtain the title compound (0.079 g) (yield: 63%).

MS m/z: 280 (M+H)⁺

$^1$H-NMR (500 MHz, CDCl$_3$) δ: 8.23 (1H, d, J=2 Hz), 7.76 (1H, dd, J=9 Hz, 2 Hz), 7.61-7.54 (4H, m), 7.09 (1H, d, J=16 Hz), 6.95 (1H, d, J=16 Hz), 6.76 (1H, d, J=9 Hz), 5.91 (1H, brs), 3.88 (2H, brs).

(3) N-[5-Methyl-3-oxo-2-(5-{(E)-2-[4-(trifluoromethyl)phenyl]ethenyl}pyridin-2-yl)-2,3-dihydro-1H-pyrazol-4-yl]acetamide

[Formula 77]

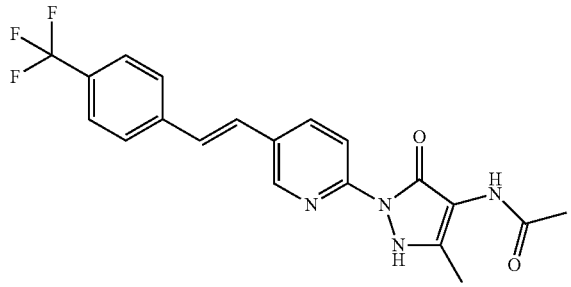

In accordance with Example 16-(3), but using 2-hydrazinyl-5-{(E)-2-[4-(trifluoromethyl)phenyl]ethenyl}pyridine instead of 6-hydrazino-N-[4-(trifluoromethyl)phenyl]nicotinamide, the title compound (0.054 g) was obtained as a white solid (yield: 47%).

MS m/z: 403 (M+H)$^+$ $^1$H-NMR (400 MHz, DMSO-d$_6$) δ: 12.01 (1H, brs), 8.95 (1H, brs), 8.65 (1H, s), 8.45 (1H, d, J=8 Hz), 8.27 (1H, d, J=8 Hz), 7.84 (2H, d, J=8 Hz), 7.76 (2H, d, J=8 Hz), 7.55-7.40 (2H, m), 2.07 (3H, s), 1.98 (3H, s).

Formulation Examples

Formulation Example 1

Injection 1.5% by weight of a compound of the Examples is stirred in 10% by volume of propylene glycol, then adjusted to a fixed volume with water for injection, and subsequently sterilized to obtain an injection.

Formulation Example 2

Hard Capsule 100 mg of a powdery compound of the Examples, 128.7 mg of lactose, 70 mg of cellulose, and 1.3 mg of magnesium stearate are mixed, and passed through 60 mesh sieve, and subsequently the resulting powders are put into 250 mg of No. 3 gelatin capsule to obtain capsules.

Formulation Example 3

Tablet 100 mg of a powdery compound of the Examples, 124 mg of lactose, 25 mg of cellulose, and 1 mg of magnesium stearate are mixed, and tabletted with a tablet-making machine to obtain tablets each having 250 mg. This tablet can be sugar-coated as necessary.

Test Example

The utility (pharmacological activity) of the compounds of the present invention was confirmed by the testing indicated below.

In vitro erythropoietin (EPO) induction activity of test compounds was evaluated using human liver cancer-derived cell line Hep3B (ATCC, Manassas, Va.). Hep3B cells were cultured overnight at 37° C. in Dulbecco's modified Eagle's medium (DMEM) in the presence of 10% fetal bovine serum (FBS) (24-well plate, 1.0×10$^5$ cells/well). After replacing with fresh DMEM (+10% FBS) containing a test compound dissolved in 0.5% dimethyl sulfoxide (DMSO) (prepared to a concentration of 12.5 µM) or a solvent control (0.5% DMSO), the cells were cultured for 32 hours at 37° C. After recovering the culture supernatant, EPO concentration in the culture supernatant was quantified using human EPO ELISA kits (StemCell Technologies). The EPO concentration obtained using each test compound was expressed as a multiple of the EPO concentration obtained using the control.

The results are shown in Table 1. The compounds of the present invention or pharmacologically acceptable salts thereof demonstrated a superior ability to produce EPO, and are useful as medicaments for treatment or prophylaxis of anemia.

TABLE 1

| Test compound | EPO concentration (multiple) |
| --- | --- |
| Control (0.5% DMSO) | 1 |
| Example 1 | 37 |
| Example 2 | 36 |
| Example 3 | 17 |
| Example 4 | 17 |
| Example 5 | 12 |
| Example 6 | 13 |
| Example 7 | 29 |
| Example 8 | 26 |
| Example 9 | 6.1 |
| Example 10 | 23 |
| Example 11 | 41 |
| Example 12 | 2.8 |
| Example 13 | 29 |
| Example 14 | 22 |
| Example 15 | 24 |
| Example 16 | 3.4 |
| Example 17 | 4.3 |
| Example 18 | 3.3 |
| Example 19 | 13 |
| Example 20 | 3.7 |
| Example 21 | 20 |
| Example 22 | 1.9 |
| Example 23 | 2.7 |
| Example 24 | 22 |
| Example 25 | 16 |
| Example 26 | 22 |
| Example 27 | 2.7 |

INDUSTRIAL APPLICABILITY

The compounds of the present invention or pharmacologically acceptable salts thereof have a superior EPO production-enhancing activity, and are useful for diseases or the like caused by decreased EPO. Specifically, the compounds of the present invention or pharmacologically acceptable salts thereof are useful as medicaments for the prophylaxis and/or treatment of anemia, preferably nephrogenic anemia, anemia of prematurity, anemia incidental to chronic diseases, anemia incidental to cancer chemotherapy, cancerous anemia, inflammation-associated anemia, or anemia incidental to congestive heart failure, more preferably anemia incidental to chronic kidney disease, and can also be used as medicaments for the prophylaxis and/or treatment of ischemic cerebrovascular disease or the like.

The invention claimed is:

1. A compound represented by the following general formula (1):

[Formula 1]

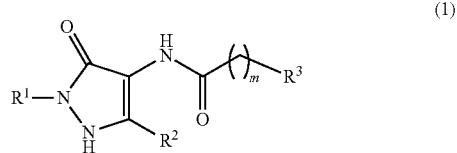

(1)

or a pharmacologically acceptable salt thereof,
wherein
R$^1$ represents a group represented by -Q$^1$, -Q$^1$-X-Q$^2$, or -Q$^1$-X-Q$^2$-Y-Q$^3$;
Q$^1$ represents a monocyclic or bicyclic aromatic heterocyclic group which may have 1 or 2 substituents independently selected from substituent group α;
substituent group α represents the group consisting of a halogen atom, a C$_1$-C$_6$ alkyl group, a halo C$_1$-C$_6$ alkyl group, a C$_1$-C$_6$ alkoxy group, a C$_3$-C$_7$ cycloalkyl group, and a 4- to 7-membered heterocycloalkyl group;
Q$^2$ represents an aromatic hydrocarbon ring group which may have 1 or 2 substituents independently selected from substituent group β, or a monocyclic aromatic heterocyclic group which may have 1 or 2 substituents independently selected from substituent group β;
substituent group β represents the group consisting of a halogen atom, a C$_1$-C$_6$ alkyl group, a halo C$_1$-C$_6$ alkyl group, a C$_1$-C$_6$ alkoxy group, a C$_3$-C$_7$ cycloalkyl group, and a cyano group;
Q$^3$ represents an aromatic hydrocarbon ring group which may have 1 or 2 substituents independently selected from substituent group γ, or a monocyclic aromatic heterocyclic group which may have 1 or 2 substituents independently selected from substituent group γ;
substituent group γ represents the group consisting of a halogen atom, a C$_1$-C$_6$ alkyl group, a halo C$_1$-C$_6$ alkyl group, a C$_1$-C$_6$ alkoxy group, a C$_3$-C$_7$ cycloalkyl group, and a cyano group;
X represents a single bond, —(CH$_2$)$_n$—, —CH═CH—, —CONH—, —NHCO—, —CONHCH$_2$—, —NHCOCH$_2$—, —CH$_2$NHCO—, —CH$_2$CONH—, —SO$_2$NH—, —CH$_2$OCH$_2$—, or —NHCH$_2$CH$_2$—;
Y represents a single bond, —O—, —(CH$_2$)$_n$—, or —O—(CH$_2$)$_n$—;
m and n each independently represents an integer from 1 to 3;
R$^2$ represents a hydrogen atom or a C$_1$-C$_6$ alkyl group; and
R$^3$ represents a hydrogen atom, a C$_1$-C$_6$ alkoxycarbonyl group, a carboxy group, an aromatic hydrocarbon ring group, or a monocyclic aromatic heterocyclic group;
with the proviso that when R$^1$ is Q$^1$, R$^2$ and R$^3$ are each hydrogen, α is a chlorine atom, and m is 1, Q$^1$ excludes a substituted pyridazine group;
with the proviso that when R$^1$ is Q$^1$, R$^2$ and R$^3$ are each hydrogen, and m is 1, Q$^1$ excludes an unsubstituted pyridine group; and
with the proviso that when R$^1$ is -Q$^1$-X-Q$^2$, X is a single bond, Q$^2$ is an unsubstituted phenyl group, m is 1, and R$^2$ and R$^3$ are each hydrogen, Q$^1$ excludes an unsubstituted pyridazine group.

2. A compound or a pharmacologically acceptable salt thereof according to claim 1, wherein R$^2$ is a hydrogen atom or a methyl group.

3. A compound or a pharmacologically acceptable salt thereof according to claim 1, wherein R$^3$ is a hydrogen atom, a methoxycarbonyl group, an ethoxycarbonyl group, a propoxycarbonyl group, a tert-butoxycarbonyl group, a carboxy group, a phenyl group, or a pyridyl group.

4. A compound or a pharmacologically acceptable salt thereof according to claim 1, wherein R$^3$ is a hydrogen atom, a tert-butoxycarbonyl group, or a carboxy group.

5. A compound or a pharmacologically acceptable salt thereof according to claim 1, wherein R$^3$ is a hydrogen atom.

6. A compound or a pharmacologically acceptable salt thereof according to claim 1, wherein m is 1 or 2.

7. A compound or a pharmacologically acceptable salt thereof according to claim 1, wherein
R$^1$ is a group represented by -Q$^1$, and
Q$^1$ is a pyridyl group, a pyrimidinyl group, a pyrazinyl group, a pyridazinyl group, a quinolyl group, an isoquinolyl group, or a quinazolinyl group which may have 1 or 2 substituents independently selected from substituent group α.

8. A compound or a pharmacologically acceptable salt thereof according to claim 1, wherein
R$^1$ is a group represented by -Q$^1$, and
Q$^1$ is a pyridyl group or a pyrimidinyl group which may have 1 or 2 substituents independently selected from substituent group α.

9. A compound or a pharmacologically acceptable salt thereof according to claim 7, wherein the substituent group α is the group consisting of a fluorine atom, a chlorine atom, a bromine atom, a methyl group, a methoxy group, a morpholinyl group, and a piperidinyl group.

10. A compound or a pharmacologically acceptable salt thereof according to claim 7, wherein the substituent group α is the group consisting of a morpholinyl group and a piperidinyl group.

11. A compound or a pharmacologically acceptable salt thereof according to claim 1, wherein
R$^1$ is a group represented by -Q$^1$-X-Q$^2$ or -Q$^1$-X-Q$^2$-Y-Q$^3$, and
Q$^1$ is a pyridyl group, a pyrimidinyl group, a pyrazinyl group, a pyridazinyl group, a quinolyl group, an isoquinolyl group, or a quinazolinyl group which may have 1 or 2 substituents independently selected from substituent group α.

12. A compound or a pharmacologically acceptable salt thereof according to claim 1, wherein
R$^1$ is a group represented by -Q$^1$-X-Q$^2$ or -Q$^1$-X-Q$^2$-Y-Q$^3$, and
Q$^1$ is a pyridyl group or a pyrimidinyl group which may have 1 or 2 substituents independently selected from substituent group α.

13. A compound or a pharmacologically acceptable salt thereof according to claim 11, wherein the substituent group α is the group consisting of a fluorine atom, a chlorine atom, a methyl group, and a methoxy group.

14. A compound or a pharmacologically acceptable salt thereof according to claim 11, wherein Q$^2$ is a phenyl group, a pyridyl group, a pyrimidinyl group, a pyrazinyl group, or a pyridazinyl group which may have 1 or 2 substituents independently selected from substituent group β.

15. A compound or a pharmacologically acceptable salt thereof according to claim 11, wherein $Q^2$ is a phenyl group or a pyridyl group which may have 1 or 2 substituents independently selected from substituent group β.

16. A compound or a pharmacologically acceptable salt thereof according to claim 14, wherein the substituent group β is the group consisting of a fluorine atom, a chlorine atom, a bromine atom, a methyl group, an ethyl group, a propyl group, an isopropyl group, a butyl group, an isobutyl group, a sec-butyl group, a tert-butyl group, a trifluoromethyl group, a cyclohexyl group, and a cyano group.

17. A compound or a pharmacologically acceptable salt thereof according to claim 14, wherein the substituent group β is the group consisting of a chlorine atom, a bromine atom, a tert-butyl group, a trifluoromethyl group, and a cyclohexyl group.

18. A compound or a pharmacologically acceptable salt thereof according to claim 11, wherein X is —CH₂—, —CH₂CH₂—, —CH═CH—, —CONH—, —CONHCH₂—, —CH₂OCH₂—, or —NHCH₂CH₂—.

19. A compound or a pharmacologically acceptable salt thereof according to claim 11, wherein X is —CH₂—, —CH₂CH₂—, —CONH—, —CONHCH₂—, or —CH₂OCH₂—.

20. A compound or a pharmacologically acceptable salt thereof according to claim 11, wherein
$R^1$ is a group represented by $-Q^1-X-Q^2-Y-Q^3$, and
$Q^3$ is a phenyl group, a pyridyl group, a pyrimidinyl group, a pyrazinyl group, or a pyridazinyl group which may have 1 or 2 substituents independently selected from substituent group γ.

21. A compound or a pharmacologically acceptable salt thereof according to claim 11, wherein
$R^1$ is a group represented by $-Q^1-X-Q^2-Y-Q^3$, and
$Q^3$ is a phenyl group or a pyridyl group which may have 1 or 2 substituents independently selected from substituent group γ.

22. A compound or a pharmacologically acceptable salt thereof according to claim 20, wherein the substituent group γ is the group consisting of a fluorine atom, a chlorine atom, a bromine atom, a methyl group, an ethyl group, a propyl group, an isopropyl group, a trifluoromethyl group, and a cyano group.

23. A compound or a pharmacologically acceptable salt thereof according to claim 20, wherein the substituent group γ is the group consisting of a chlorine atom, a bromine atom, a trifluoromethyl group, and a cyano group.

24. A compound or a pharmacologically acceptable salt thereof according to claim 11, wherein Y is a single bond or —O—.

25. A compound or a pharmacologically acceptable salt thereof selected from the following:
6-(4-acetamido-5-oxo-2,5-dihydro-1H-pyrazol-1-yl)-N-(4-cyclohexylphenyl)nicotinamide,
6-(4-acetamido-5-oxo-2,5-dihydro-1H-pyrazol-1-yl)-N-(4-tert-butylphenyl)nicotinamide,
6-(4-acetamido-5-oxo-2,5-dihydro-1H-pyrazol-1-yl)-N-(3-tert-butylphenyl)nicotinamide,
6-(4-acetamido-5-oxo-2,5-dihydro-1H-pyrazol-1-yl)-N-[4-(trifluoromethyl)phenyl]nicotinamide,
6-(4-acetamido-5-oxo-2,5-dihydro-1H-pyrazol-1-yl)-N-(4-chlorophenyl)nicotinamide,
N-[2-(6-morpholin-4-ylpyrimidin-4-yl)-3-oxo-2,3-dihydro-1H-pyrazol-4-yl]acetamide,
N-[3-oxo-2-(6-piperidin-1-ylpyrimidin-4-yl)-2,3-dihydro-1H-pyrazol-4-yl]acetamide,
N-(2-{5-[(benzyloxy)methyl]pyridin-2-yl}-3-oxo-2,3-dihydro-1H-pyrazol-4-yl)acetamide,
N-(3-oxo-2-{6-[(2-phenylethyl)amino]pyrimidin-4-yl}-2,3-dihydro-1H-pyrazol-4-yl)acetamide,
N-(2-{4-[(benzyloxy)methyl]pyridin-2-yl}-3-oxo-2,3-dihydro-1H-pyrazol-4-yl)acetamide,
6-(4-acetamido-5-oxo-2,5-dihydro-1H-pyrazol-1-yl)-N-(biphenyl-3-ylmethyl)nicotinamide,
6-(4-acetamido-5-oxo-2,5-dihydro-1H-pyrazol-1-yl)-N-[(2'-cyanobiphenyl-4-ylmethyl)]nicotinamide,
N-[2-(5-{[(2'-cyanobiphenyl-4-yl)methoxy]methyl}pyridin-2-yl)-3-oxo-2,3-dihydro-1H-pyrazol-4-yl]acetamide,
N-(2-{5-[(biphenyl-4-ylmethoxy)methyl]pyridin-2-yl}-3-oxo-2,3-dihydro-1H-pyrazol-4-yl)acetamide,
N-(2-{5-[(biphenyl-3-ylmethoxy)methyl]pyridin-2-yl}-3-oxo-2,3-dihydro-1H-pyrazol-4-yl)acetamide,
6-(4-acetamido-3-methyl-5-oxo-2,5-dihydro-1H-pyrazol-1-yl)-N-[4-(trifluoromethyl)phenyl]nicotinamide,
6-(4-acetamido-3-methyl-5-oxo-2,5-dihydro-1H-pyrazol-1-yl)-N-(4-chlorophenyl)nicotinamide,
6-(4-acetamido-3-methyl-5-oxo-2,5-dihydro-1H-pyrazol-1-yl)-N-(4-bromophenyl)nicotinamide,
6-(4-acetamido-3-methyl-5-oxo-2,5-dihydro-1H-pyrazol-1-yl)-N-(4-tert-butylphenyl)nicotinamide,
6-(4-acetamido-3-methyl-5-oxo-2,5-dihydro-1H-pyrazol-1-yl)-N-(6-phenylpyridin-3-yl)nicotinamide,
N-[2-(5-{[(2'-cyanobiphenyl-4-yl)methoxy]methyl}pyridin-2-yl)-5-methyl-3-oxo-2,3-dihydro-1H-pyrazol-4-yl]acetamide,
tert-butyl 4-[(5-methyl-3-oxo-2-{5-[(6-phenylpyridyl-3-yl)carbamoyl]pyridin-2-yl}-2,3-dihydro-1H-pyrazol-4-yl)amino]-4-oxobutanoate,
4-[(5-methyl-3-oxo-2-{5-[(6-phenylpyridyl-3-yl)carbamoyl]pyridin-2-yl}-2,3-dihydro-1H-pyrazol-4-yl)amino]-4-oxobutanoic acid,
N-{5-methyl-3-oxo-2-[5-({[4-(trifluoromethyl)benzyl]oxy}methyl)pyridin-2-yl]-2,3-dihydro-1H-pyrazol-4-yl}acetamide,
N-(5-methyl-3-oxo-2-{5-[4-(trifluoromethyl)benzyl]pyridin-2-yl}-2,3-dihydro-1H-pyrazol-4-yl)acetamide,
N-[5-methyl-3-oxo-2-(5-{2-[4-(trifluoromethyl)phenyl]ethyl}pyridin-2-yl)-2,3-dihydro-1H-pyrazol-4-yl]acetamide, and
N-[5-methyl-3-oxo-2-(5-{(E)-2-[4-(trifluoromethyl)phenyl]ethenyl}pyridin-2-yl)-2,3-dihydro-1H-pyrazol-4-yl]acetamide.

26. A compound or a pharmacologically acceptable salt thereof selected from the following:
6-(4-acetamido-5-oxo-2,5-dihydro-1H-pyrazol-1-yl)-N-(4-cyclohexylphenyl)nicotinamide,
6-(4-acetamido-5-oxo-2,5-dihydro-1H-pyrazol-1-yl)-N-(4-tert-butylphenyl)nicotinamide,
6-(4-acetamido-5-oxo-2,5-dihydro-1H-pyrazol-1-yl)-N-(3-tert-butylphenyl)nicotinamide,
6-(4-acetamido-5-oxo-2,5-dihydro-1H-pyrazol-1-yl)-N-[4-(trifluoromethyl)phenyl]nicotinamide,
6-(4-acetamido-5-oxo-2,5-dihydro-1H-pyrazol-1-yl)-N-(4-chlorophenyl)nicotinamide,
N-[2-(6-morpholin-4-ylpyrimidin-4-yl)-3-oxo-2,3-dihydro-1H-pyrazol-4-yl]acetamide,
N-[3-oxo-2-(6-piperidin-1-ylpyrimidin-4-yl)-2,3-dihydro-1H-pyrazol-4-yl]acetamide,
N-(2-{5-[(benzyloxy)methyl]pyridin-2-yl}-3-oxo-2,3-dihydro-1H-pyrazol-4-yl)acetamide, N-(2-{4-[(benzyloxy)methyl]pyridin-2-yl}-3-oxo-2,3-dihydro-1H-pyrazol-4-yl)acetamide,
6-(4-acetamido-5-oxo-2,5-dihydro-1H-pyrazol-1-yl)-N-(biphenyl-3-ylmethyl)nicotinamide,
N-[2-(5-{[(2'-cyanobiphenyl-4-yl)methoxy]methyl}pyridin-2-yl)-3-oxo-2,3-dihydro-1H-pyrazol-4-yl]acetamide,
N-(2-{5-[(biphenyl-4-ylmethoxy)methyl]pyridin-2-yl}-3-oxo-2,3-dihydro-1H-pyrazol-4-yl)acetamide,
N-(2-{5-[(biphenyl-3-ylmethoxy)methyl]pyridin-2-yl}-3-oxo-2,3-dihydro-1H-pyrazol-4-yl)acetamide,
6-(4-acetamido-3-methyl-5-oxo-2,5-dihydro-1H-pyrazol-1-yl)-N-(4-tert-butylphenyl)nicotinamide,
N-[2-(5-{[(2'-cyanobiphenyl-4-yl)methoxy]methyl}pyridin-2-yl)-5-methyl-3-oxo-2,3-dihydro-1H-pyrazol-4-yl]acetamide,
N-{5-methyl-3-oxo-2-[5-({[4-(trifluoromethyl)benzyl]oxy}methyl)pyridin-2-yl]-2,3-dihydro-1H-pyrazol-4-yl}acetamide,
N-(5-methyl-3-oxo-2-{5-[4-(trifluoromethyl)benzyl]pyridin-2-yl}-2,3-dihydro-1H-pyrazol-4-yl)acetamide, and
N-[5-methyl-3-oxo-2-(5-{2-[4-(trifluoromethyl)phenyl]ethyl}pyridin-2-yl)-2,3-dihydro-1H-pyrazol-4-yl]acetamide.

27. A pharmaceutical composition containing as an active ingredient a compound or a pharmacologically acceptable salt thereof according to claim 1.

28. A pharmaceutical composition according to claim 27, for the treatment of anemia.

29. A pharmaceutical composition according to claim 27, for producing erythropoietin.

30. A method for producing erythropoietin, comprising: administering a pharmacologically effective amount of a compound or a pharmacologically acceptable salt thereof according to claim 1 to a human.

31. A method for the treatment of a disease caused by decreased erythropoietin (EPO), comprising: administering a pharmacologically effective amount of a compound or a pharmacologically acceptable salt thereof according to claim 1 to a human.

32. A method according to claim 31, wherein the disease is anemia.

33. A pharmaceutical composition according to claim 27, for the treatment of a disease caused by decreased erythropoietin (EPO).

34. A pharmaceutical composition according to claim 33, wherein the disease is anemia.

* * * * *